US011241478B2

(12) United States Patent
Chetkovich et al.

(10) Patent No.: US 11,241,478 B2
(45) Date of Patent: Feb. 8, 2022

(54) ADENOVIRUS-ASSOCIATED VIRAL VECTORS FOR EXPRESSING VARIANTS OF TETRATRICOPEPTIDE REPEAT (TPR)-CONTAINING RAB8B INTERACTING (TRIP8B) PROTEIN IN NEURONS AND USES THEREOF FOR TREATING MAJOR DEPRESSIVE DISORDER (MDD)

(71) Applicant: Northwestern University, Evanston, IL (US)

(72) Inventors: Dane M. Chetkovich, Chicago, IL (US); Ye Han, Lisle, IL (US); Kyle Lyman, Evanston, IL (US); Robert John Heuermann, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/166,820

(22) Filed: Oct. 22, 2018

(65) Prior Publication Data
US 2019/0038707 A1 Feb. 7, 2019

Related U.S. Application Data

(63) Continuation-in-part of application No. PCT/US2017/028931, filed on Apr. 21, 2017.

(60) Provisional application No. 62/326,464, filed on Apr. 22, 2016.

(51) Int. Cl.
| | |
|---|---|
| *C12N 15/63* | (2006.01) |
| *C07H 21/04* | (2006.01) |
| *A61K 38/16* | (2006.01) |
| *C07K 14/47* | (2006.01) |
| *A61P 25/24* | (2006.01) |
| *G01N 33/68* | (2006.01) |
| *A61K 38/00* | (2006.01) |

(52) U.S. Cl.
CPC .............. *A61K 38/16* (2013.01); *A61P 25/24* (2018.01); *C07K 14/47* (2013.01); *C12N 15/63* (2013.01); *G01N 33/68* (2013.01); *A61K 38/00* (2013.01); *C07H 21/04* (2013.01); *C12N 2750/14141* (2013.01)

(58) Field of Classification Search
CPC ................ C12N 15/86; C12N 15/8645; C12N 2750/14141; C07H 21/04
See application file for complete search history.

(56) References Cited

U.S. PATENT DOCUMENTS

2009/0221610 A1   9/2009   Arnsten et al.

OTHER PUBLICATIONS

Bryan et al., 2013, http://www.elsevierblogs.com/currentcomments/?p=962, Implications of protein fold switching, p. 1-4.*
Maqbool et al., 2015, Biochemical Society Transactions, vol. 43, No. 5, p. 1011-1017.*
Cruz et al., 2017, Methods in Molecular Biology, vol. 1654, Chapter 5, pp. 55-75.*
Aschauer DF, Kreuz S, Rumpel S. Analysis of Transduction Efficiency, Tropism and Axonal Transport of AAV Serotypes 1, 2, 5, 6, 8 and 9 in the Mouse Brain. PLoS One 2013; 8: e76310.
Biel M, Wahl-Schott C, Michalakis S, Zong X. Hyperpolarization-activated cation channels: from genes to function. Physiol Rev 2009; 89: 847-885.
Cai X, Kallarackal AJ, Kvarta MD, Goluskin S, Gaylor K, Bailey AM et al. Local potentiation of excitatory synapses by serotonin and its alteration in rodent models of depression. Nat Neurosci 2013; 16: 464-472.
Cao JL, Covington HE, Friedman AK, Wilkinson MB, Walsh JJ, Cooper DC et al. Mesolimbic Dopamine Neurons in the Brain Reward Circuit Mediate Susceptibility to Social Defeat and Antidepressant Action. J Neurosci 2010; 30: 16453-16458.
Chung WK, Shin M, Jaramillo TC, Leibel RL, LeDuc CA, Fischer SG et al. Absence epilepsy in apathetic, a spontaneous mutant mouse lacking the h channel subunit, HCN2. Neurobiol Dis 2009; 33: 499-508.
Duman RS, Aghajanian GK. Synaptic Dysfunction in Depression: Potential Therapeutic Targets. Science 2012; 338: 68-72.
Friedman AK, Walsh JJ, Juarez B, Ku SM, Chaudhury D, Wang J et al. Enhancing depression mechanisms in midbrain dopamine neurons achieves homeostatic resilience. Science 2014; 344: 313-319.
Giesbrecht CJ, Mackay JP, Silveira HB, Urban JH, Colmers WF. Countervailing Modulation of Ih by Neuropeptide Y and Corticotrophin-Releasing Factor in Basolateral Amygdala As a Possible Mechanism for Their Effects on Stress-Related Behaviors. J Neurosci 2010; 30: 16970-16982.

(Continued)

*Primary Examiner* — Shin Lin Chen
(74) *Attorney, Agent, or Firm* — Quarles & Brady LLP

(57) ABSTRACT

Disclosed are methods and compositions for treating a subject having a neurological disorder such as major depressive disorder (MDD). The methods and compositions may be utilized in order to inhibit trafficking of hyperpolarization-activated cyclic nucleotide gated (HCN) channels or subunits thereof, in some embodiments, by inhibiting an interaction between the HCN channels or the subunits thereof and an auxiliary protein or a chaperone protein for the HCN channels or the subunits thereof such as tetratricopeptide repeat (TPR)-containing Rab8b interacting (TRIP8b) protein or a variant thereof. The HCN channels of the disclosed methods may comprise, for example, HCN1 subunits, HCN2 subunits, or a combination thereof. In the disclosed methods, trafficking of the HCN channels or subunits preferably results in inhibiting distal dendritic enrichment of HCN1 and HCN2 in pyramidal neurons of hippocampal area CA1.

3 Claims, 17 Drawing Sheets

Specification includes a Sequence Listing.

(56) References Cited

OTHER PUBLICATIONS

Han Y, Noam Y, Lewis AS, Gallagher JJ, Wadman WJ, Baram TZ et al. Trafficking and gating of hyperpolarization-activated cyclic nucleotide-gated channels are regulated by interaction with tetratricopeptide repeat-containing Rab8b-interacting protein (TRIP8b) and cyclic AMP at distinct sites. J Biol Chem 2011; 286: 20823-20834.

Heuermann RJ, Jaramillo TC, Ying S-W, Suter BA, Lyman KA, Han Y et al. Reduction of thalamic and cortical Ih by deletion of TRIP8b produces a mouse model of human absence epilepsy. Neurobiol Dis 2016; 85: 81-92.

Joëls M, Baram TZ. The neuro-symphony of stress. Nat Rev Neurosci 2009; 10: 459-466.

Kallarackal AJ, Kvarta MD, Cammarata E, Jaberi L, Cai X, Bailey AM et al. Chronic Stress Induces a Selective Decrease in AMPA Receptor-Mediated Synaptic Excitation at Hippocampal Temporoammonic-CA1 Synapses. J Neurosci 2013; 33: 15669-15674.

Kessler RC, Berglund P, Dernier O, Jin R, Merikangas KR, Walters EE. Lifetime prevalence and age-of-onset distributions of DSM-IV disorders in the National Comorbidity Survey Replication. Arch Gen Psychiatry 2005; 62: 593-602.

Kim CS, Chang PY, Johnston D. Enhancement of dorsal hippocampal activity by knockdown of HCN1 channels leads to anxiolytic- and antidepressant-like behaviors. Neuron 2012; 75: 503-516.

Krishnan V, Nestler EJ. The molecular neurobiology of depression. Nature 2008; 455: 894-902.

Lépine J-P, Briley M. The increasing burden of depression. Neuropsychiatr Dis Treat 2011; 7: 3-7.

Lewis AS, Schwartz E, Chan CS, Noam Y, Shin M, Wadman WJ et al. Alternatively spliced isoforms of TRIP8b differentially control h channel trafficking and function. J Neurosci 2009; 29: 6250-6265.

Lewis AS, Vaidya SP, Blaiss CA, Liu Z, Stoub TR, Brager DH et al. Deletion of the hyperpolarization-activated cyclic nucleotide-gated channel auxiliary subunit TRIP8b impairs hippocampal Ih localization and function and promotes antidepressant behavior in mice. J Neurosci 2011; 31: 7424-7440.

Magee JC. Dendritic hyperpolarization-activated currents modify the integrative properties of hippocampal CA1 pyramidal neurons. J Neurosci 1998; 18: 7613-7624.

Magee J. Dendritic Ih normalizes temporal summation in hippocampal CA1 neurons. Nat Neurosci 1999; 2: 848-848.

Newport DJ, Carpenter LL, McDonald WM, Potash JB, Tohen M, Nemeroff CB et al. Ketamine and other NMDA antagonists: early clinical trials and possible mechanisms in depression. Am J Psychiatry 2015; 172: 950-966.

Papakostas GI, Ionescu DF. Towards new mechanisms: an update on therapeutics for treatment-resistant major depressive disorder. Mol Psychiatry 2015; 20: 1142-1150.

Piskorowski R, Santoro B, Siegelbaum SA. TRIP8b splice forms act in concert to regulate the localization and expression of HCN1 channels in CA1 pyramidal neurons. Neuron 2011; 70: 495-509.

Qiu DL, Chu CP, Shirasaka T, Tsukino H, Nakao H, Kato K et al. Corticotrophin-releasing factor augments the IH in rat hypothalamic paraventricular nucleus parvocellular neurons in vitro. J Neurophysiol 2005; 94: 226-234.

Russo SJ, Nestler EJ. The brain reward circuitry in mood disorders. Nat Rev Neurosci 2013; 14: 609-625.

Santoro B, Hu L, Liu H, Saponaro A, Pian P, Piskorowski RA et al. TRIP8b regulates HCN1 channel trafficking and gating through two distinct C-terminal interaction sites. J Neurosci 2011; 31: 4074-4086.

Santoro B, Piskorowski RA, Pian P, Hu L, Liu H, Siegelbuam SA. TRIP8b splice variants form a family of auxiliary subunits that regulate gating and trafficking of HCN channels in the brain. Neuron 2009; 62: 802-813.

Saponaro A, Pauleta SR, Cantini F, Matzapetakis M, Hammann C, Donadoni C et al. Structural basis for the mutual antagonism of cAMP and TRIP8b in regulating HCN channel function. Proc Natl Acad Sci U S A 2014; 111: 14577-14582.

Shin M, Chetkovich DM. Activity-dependent regulation of h channel distribution in hippocampal CA1 pyramidal neurons. J Biol Chem 2007; 282: 33168-33180.

Shin M, Simkin D, Suyeoka GM, Chetkovich DM. Evaluation of HCN2 abnormalities as a cause of juvenile audiogenic seizures in Black Swiss mice. Brain Res 2006; 1083: 14-20.

Stepan J, Hladky F, Uribe A, Holsboer F, Schmidt MV, Eder M. High-Speed imaging reveals opposing effects of chronic stress and antidepressants on neuronal activity propagation through the hippocampal trisynaptic circuit. Front Neural Circuits 2015; 9: 819.

Tsay D, Dudman JT, Siegelbaum SA. HCN1 channels constrain synaptically evoked Ca2+ spikes in distal dendrites of CA1 pyramidal neurons. Neuron 2007; 56: 1076-1089.

Wahl-Schott C, Biel M. HCN channels: structure, cellular regulation and physiological function. Cell Mol Life Sci 2009; 66: 470-494.

Zolles G, Wenzel D, Bildl W, Schulte U, Hofmann A, Muller CS et al. Association with the auxiliary subunit PEX5R/Trip8b controls responsiveness of HCN channels to cAMP and adrenergic stimulation. Neuron 2009; 62: 814-825.

Han Y. et al. Identification of Small-Molecule Inhibitors of Hyperpolarization-Activated Cyclic Nucleotide-Gated Channels. Journal of BBiomolecular Screening,Oct. 2015, 20(9), p. 1-8, especially abstract, p. 2-4.

Heuermann R. J. The Role of HCN Channels and TRIP8b in Depression and Epilepsy. A Dissertation submitted to the graduate school in partial fulfillment of the requirements for the degree doctor of philosophy, 2015, p. 2-3, abstract.

International Search Report and Written Opinion for PCT/US2017/028931 dated Aug. 14, 2017.

International Preliminary Reporton Patentability for PCT/US2017/028931 dated Nov. 1, 2018.

Heuermann, R.J. The Role of HCN Channels and TRIP8b in Depression and Epilepsy. A Dissertation submitted to the graduate school in partial fulfillment of the requirements for the degree doctor of philosophy, 2015. 154 pages.

* cited by examiner

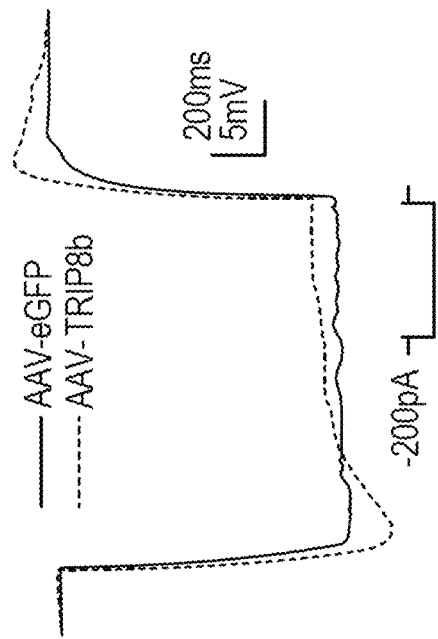
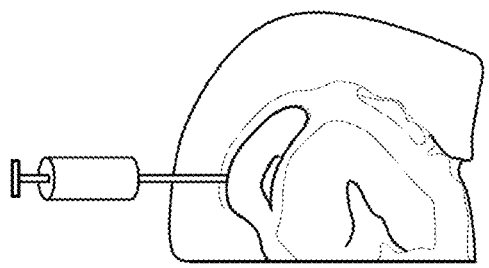
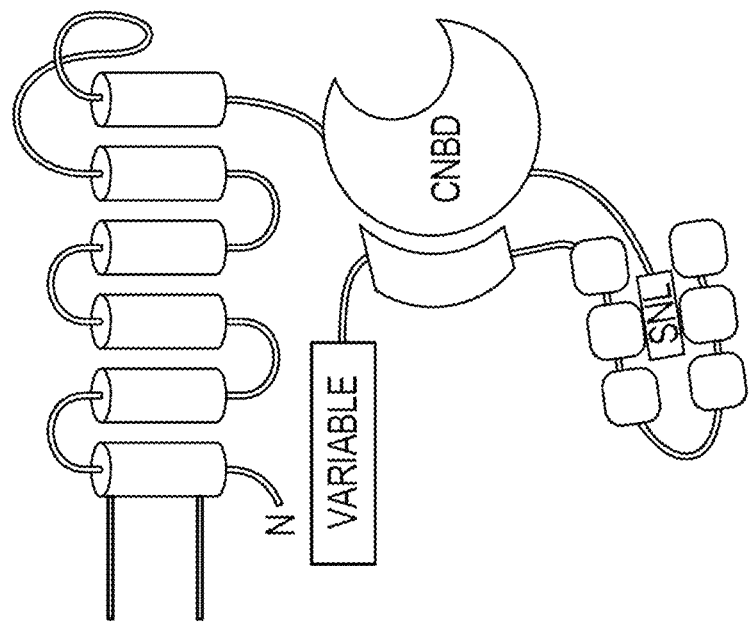
FIG. 1C
FIG. 1B
FIG. 1A

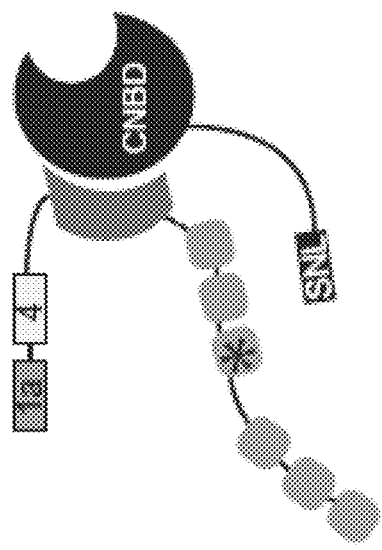
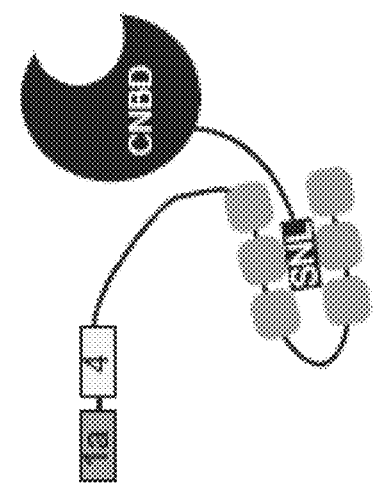
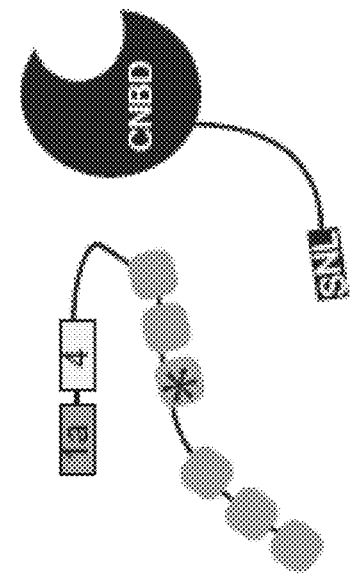
FIG. 3A
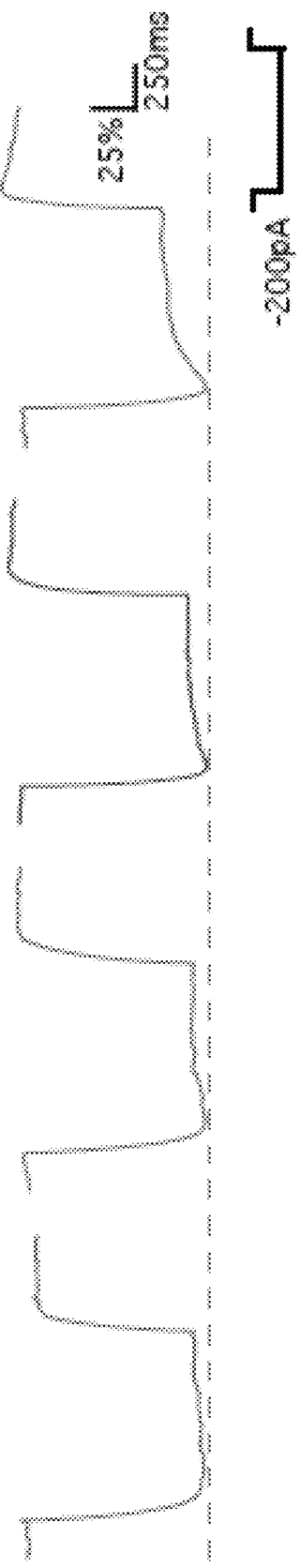
FIG. 3B

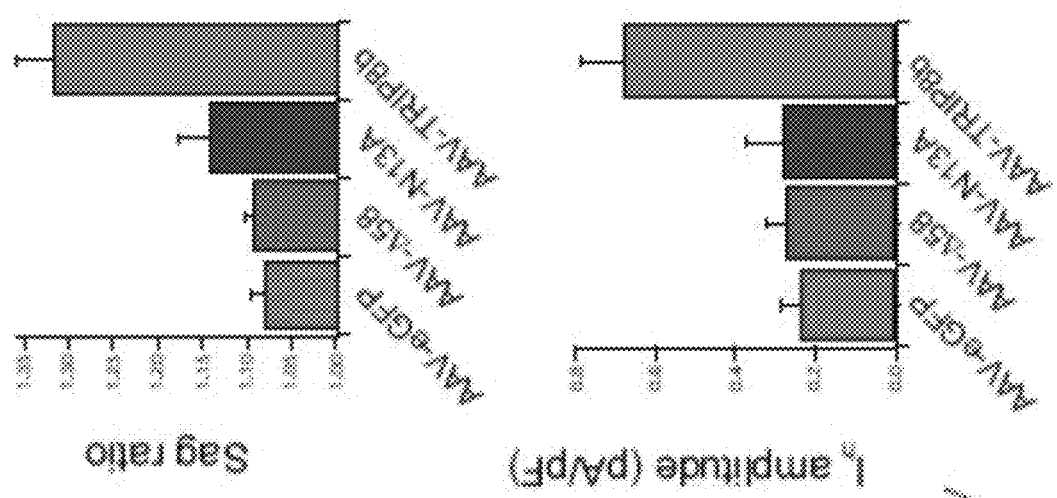
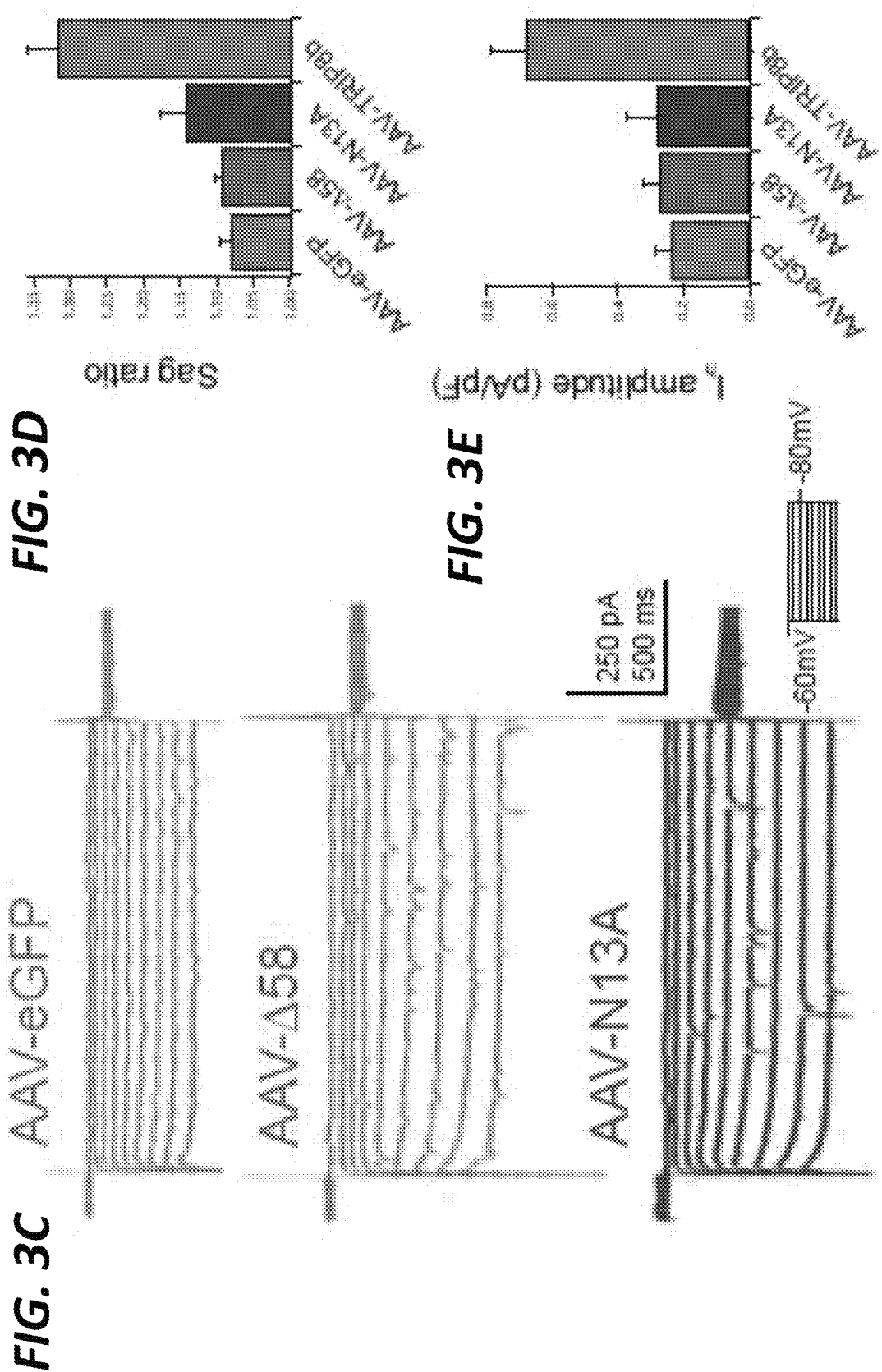
FIG. 3C
FIG. 3D
FIG. 3E

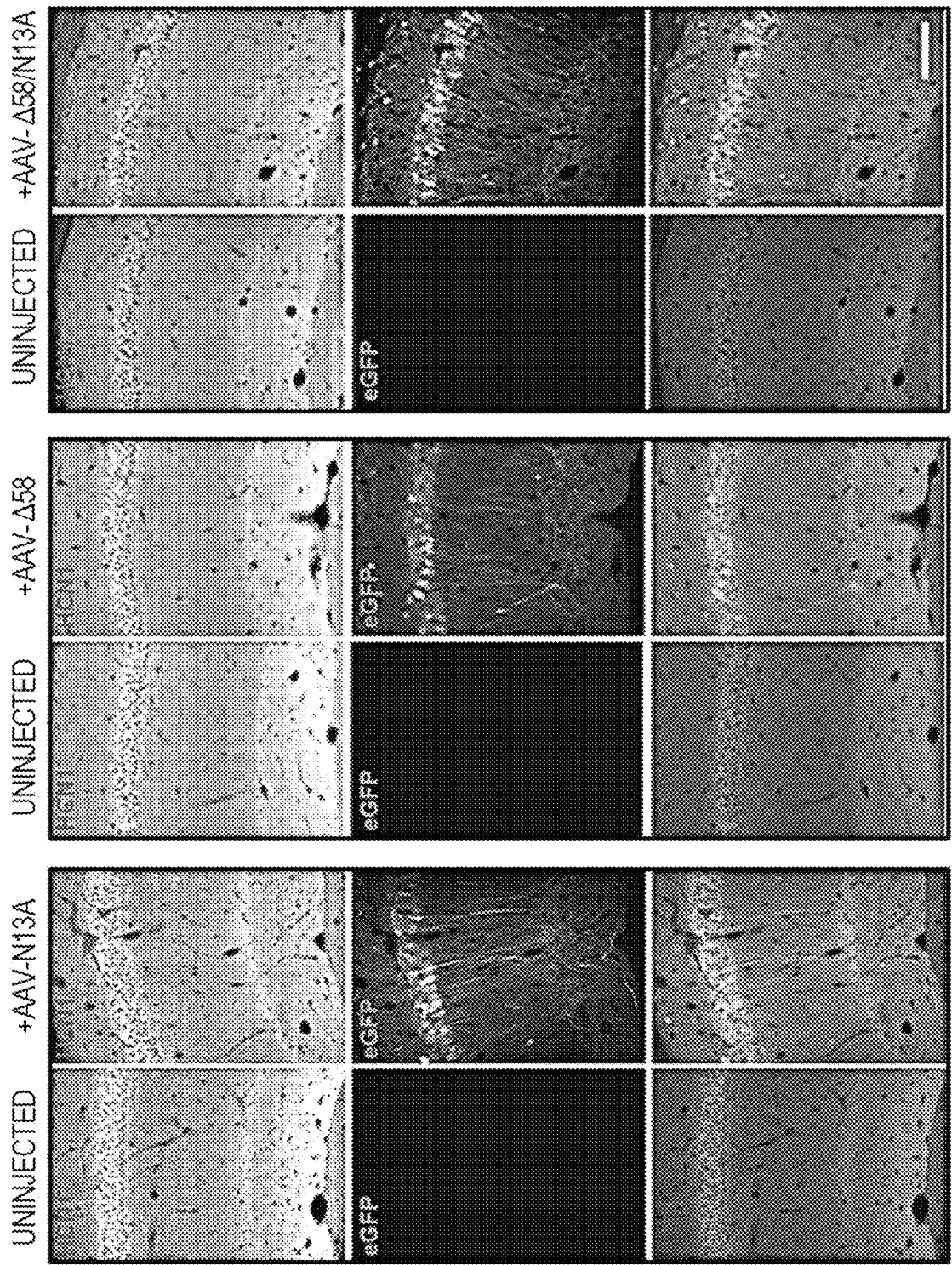

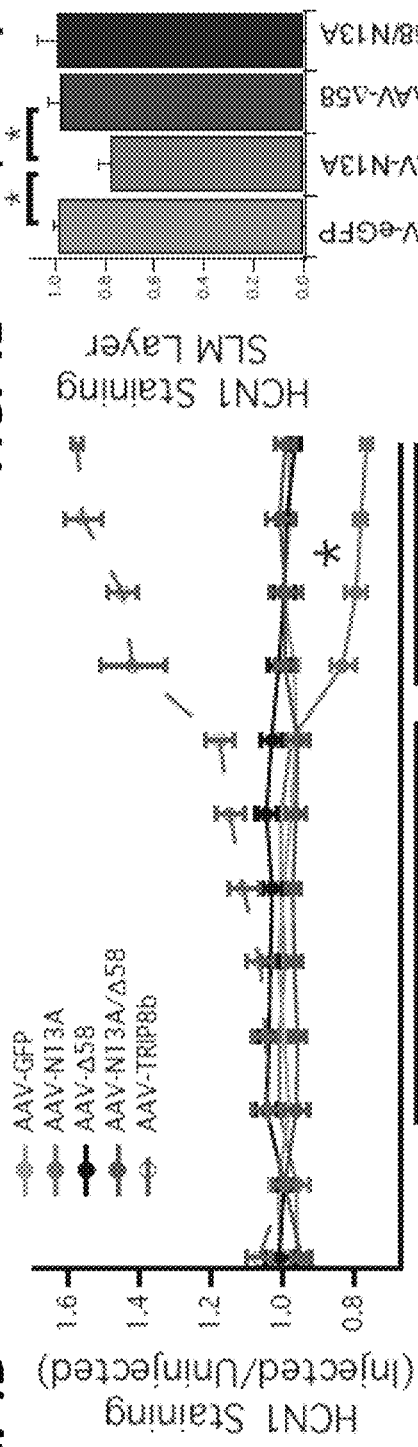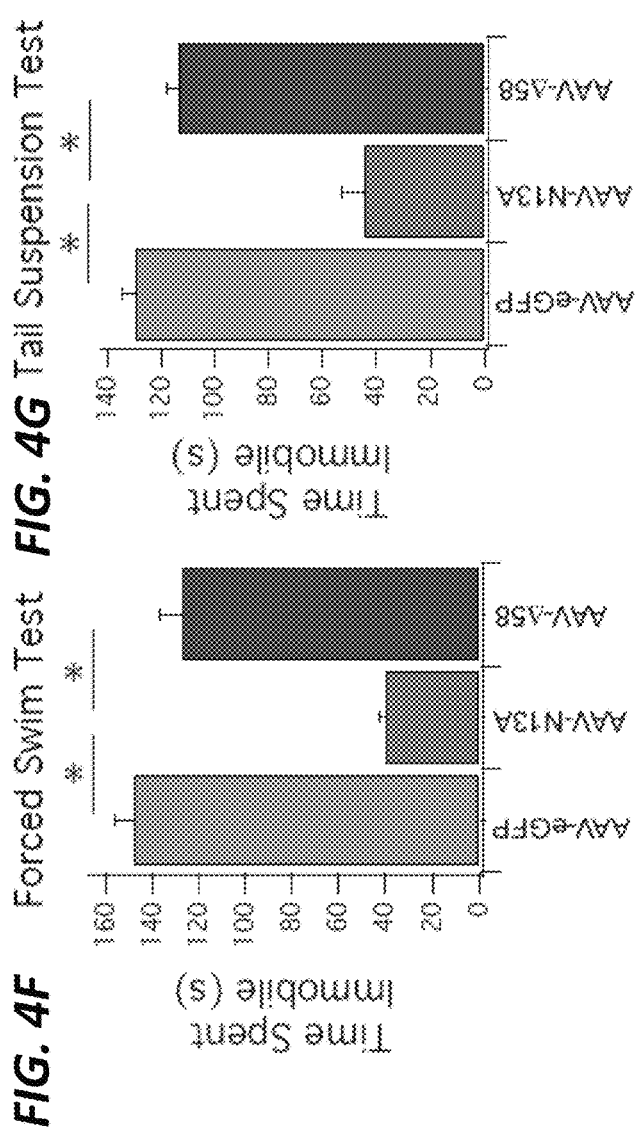

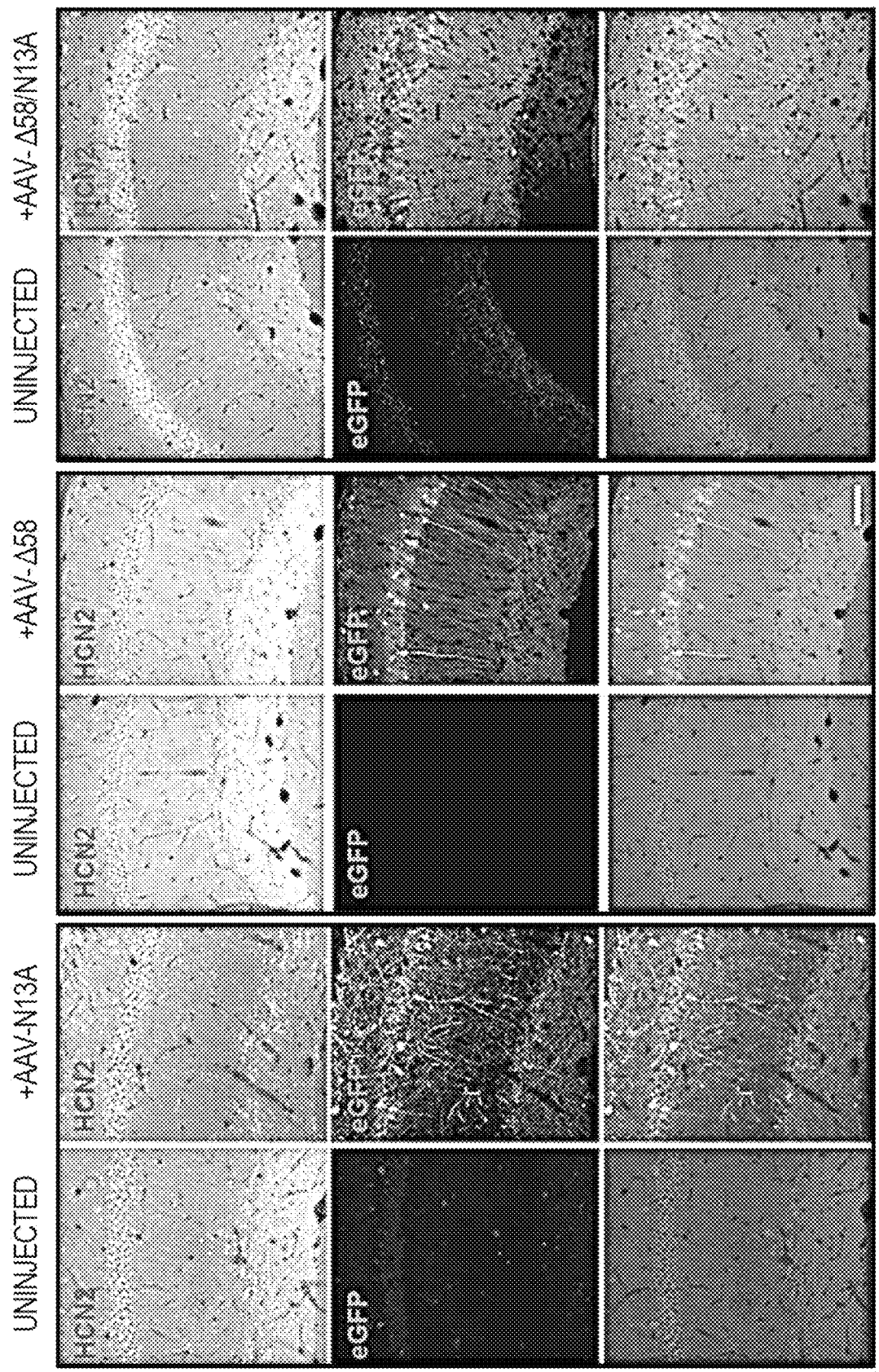

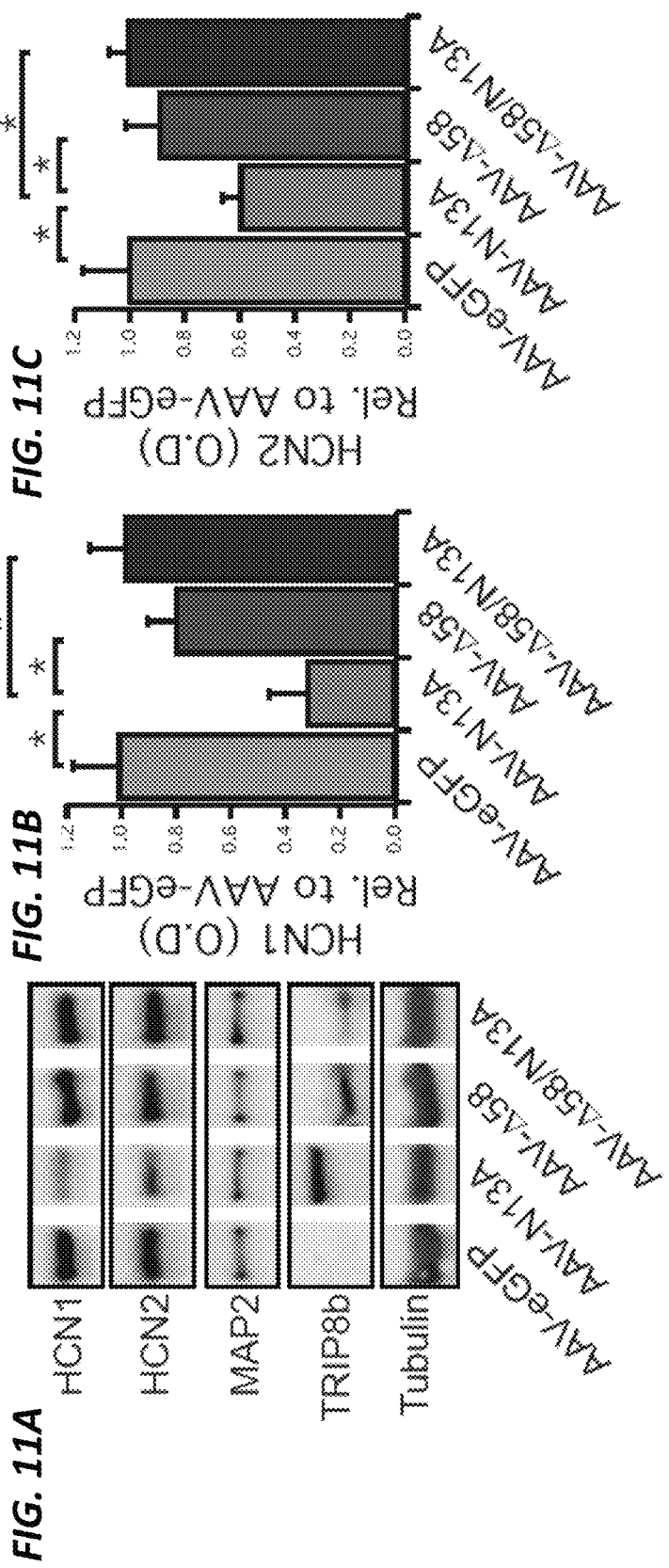

ADENOVIRUS-ASSOCIATED VIRAL VECTORS FOR EXPRESSING VARIANTS OF TETRATRICOPEPTIDE REPEAT (TPR)-CONTAINING RAB8B INTERACTING (TRIP8B) PROTEIN IN NEURONS AND USES THEREOF FOR TREATING MAJOR DEPRESSIVE DISORDER (MDD)

CROSS-REFERENCE TO RELATED PATENT APPLICATIONS

The present application is a continuation-in-part of International Application No. PCT/US2017/028931, filed on Apr. 21, 2017, and published on Oct. 26, 2017, as WO 2017/185027 which application claims the benefit of priority under 35 U.S.C. § 119(e) to U.S. Provisional Patent Application No. 62/326,464, filed on Apr. 22, 2016, the contents of which are incorporated herein by reference in their entireties.

BACKGROUND

The field of the invention relates to methods and compositions for treating neurological disorders. In particular, the field of the invention relates to gene therapy and small molecules for treating major depressive disorder by inhibiting trafficking of hyperpolarization-activated cyclic nucleotide gated (HCN) channels or subunits thereof.

Major depressive disorder (MDD) is a highly prevalent public health problem. Although there are many drugs available to treat patients with MDD, nearly all of the drugs target the same chemicals in the brain and have limited therapeutic efficacy. In order to better treat patients with MDD, we have developed a gene therapy based treatment that targets a distinct therapeutic mechanism. Our therapy could be used to treat patients who are refractory to existing antidepressants or could be used in combination with pharmaceutical therapies. In addition, the therapeutic mechanism that we have targeted with gene therapy also may be targeted with small molecule inhibitors.

SUMMARY

Disclosed are methods and compositions for treating a subject having a neurological disorder such as major depressive disorder (MDD). The methods and compositions disclosed herein may be utilized in order to inhibit trafficking of hyperpolarization-activated cyclic nucleotide gated (HCN) channels or subunits thereof. The HCN channels of the disclosed methods may comprise, for example, HCN1 subunits, HCN2 subunits, HCN3 subunits, HCN4 subunits, or a combination thereof. In the disclosed methods, trafficking of the HCN channels or subunits may result in inhibiting distal dendritic enrichment of HCN1 and HCN2 in pyramidal neurons of hippocampal area CA1

BRIEF DESCRIPTION OF THE FIGURES

FIG. 1A, FIG. 1B, FIG. 1C, FIG. 1D, FIG. 1E, and FIG. IF together illustrate that viral expression of TRIP8b is sufficient to rescue $I_h$. FIG. 1A. Schematic of TRIP8b interacting with a single HCN pore forming subunit. The N-terminal interaction occurs between the CNBD of HCN and an acidic stretch of amino acids in TRIP8b, schematized by a red shape. The C-terminal tail interaction occurs between the TPR domains of TRIP8b in gray and the 'SNL' tripeptide of HCN1, 2, and 4. The variably spliced N terminus of TRIP8b is represented by a green rectangle. FIG. 1B. Schematic showing virus injection site. Coronal brain image generated using the Allen Mouse Brain Atlas{Lein: 2007jn}. FIG. 1C. Whole cell somatic recordings were performed from eGFP positive CA1 pyramidal neurons four weeks after bilateral viral injection into TRIP8b KO mice. Representative traces are shown during hyperpolarizing current injection to highlight the $I_h$ current. FIG. 1D. Quantification of sag ratio. For reference, WT mice injected with AAV-eGFP are also shown (WT 1.23±0.02, n=8). Recordings from eGFP positive cells in TRIP8b KO mice were recorded four weeks after injection (AAV-eGFP: 1.07±0.01, n=9, AAV-TRIP8b: 1.27±0.04, n=8). A one way ANOVA comparing the magnitude of the sag ratio was significant (F(2,22)=11.64, p<0.001). Tukey's post hoc tests found a difference between AAV-eGFP infected WT cells and AAV-eGFP infected TRIP8b KO cells and a difference between AAV-eGFP infected TRIP8b KO cells and AAV-TRIP8b infected TRIP8b KO cells (p<0.05). FIG. 1E. Quantification of $I_h$ amplitude from somatic voltage clamp recordings from TRIP8b KO animals injected with the indicated viral construct (AAV-eGFP: 0.24±0.05 pA/pF, n=9, AAV-TRIP8b: 0.68±0.10 pA/pF, n=7). AAV-eGFP injected wild type mice are included for reference (0.67±0.11 pA, n=8). A one way ANOVA comparing the magnitude of the current was significant (F(2,21)=7.92, p<0.01).

FIG. 2A Low power composite image of TRIP8b KO animals unilaterally injected with AAV-TRIP8b. Uninjected hemisphere (left) shows absence of TRIP8b (red, top panel) and weak hippocampal HCN gradients (green, middle and lower panels). Injected hemisphere (right) shows restoration of the distal dendritic enrichment of TRIP8b, HCN1, and HCN2. SO: Stratum oriens, SP: Stratum pyramidale, SR: Stratum radiatum, SLM: Stratum lacunosum moleculare. Scale bar represents 200 µm. FIG. 2B Quantification of HCN1 channel expression after viral rescue. A value of '1' represents no change in staining of HCN1 relative to the uninjected hemisphere. Asterisk denotes comparison of HCN1 staining in the SLM (AAV-eGFP: 0.98±0.01 n=6, AAV-TRIP8b=1.52±0.05 n=4, t=23.81, p<0.001). FIG. 2C and FIG. 2D. TRIP8b KO mice bilaterally injected with AAV-TRIP8b showed more immobility time on forced swim test and tail suspension test (FST) relative to AAV-eGFP injected controls. Injection of AAV-TRIP8b increased the immobility time on TST (AAV-eGFP=132±20.9 sec, AAV-TRIP8b 166.16±26.5 sec, t=2.47, p<0.05) and FST (AAV-eGFP=77.3±11.2 sec, AAV-TRIP8b=142.8±20.1 sec, t=6.96, p<0.05), indicating a reversal of the increase in antidepressant-like behavioral effects of TRIP8b KO mice (n=6,6). For comparison, uninjected wild type mice and uninjected TRIP8b KO mice are also shown to highlight the increase in antidepressant-like behavior for both TST (WT=191.8±17.6 sec, TRIP8b KO=134.8±23.4 sec, t=4.47, p<0.05) and FST (WT=142.4±21.8 sec, TRIP8b KO=85.6±9.93 sec, t=5.72, p<0.05) (n=6,5). Note that the comparison between AAV-eGFP and AAV-TRIP8b is distinct from the comparison between wild type and TRIP8b KO mice because the AAV-eGFP/AAV-TRIP8b were both subject to bilateral viral injections while the other groups were not. *P<0.05 two tail unpaired T test. All error bars represent±standard error of the mean and are described above as mean±s.e.m.

FIG. 3A, FIG. 3B, FIG. 3C, FIG. 3D, and FIG. 3E together illustrate that loss of either TRIP8b-HCN binding site blocks viral rescue of $I_h$. FIG. 3A. Schematic of mutant TRIP8b isoforms used showing predicted results of mutating either binding site. FIG. 3B. Somatic whole cell recordings were performed from TRIP8b KO mice four weeks after bilateral injection with the indicated mutant construct. Representative traces are shown during hyperpolarizing current injections to demonstrate $I_h$ current. Note that to facilitate direct comparison of the sag ratio all traces were normalized to the maximum voltage deflection occurring in response to a 1 second long −200 pA current injection. FIG. 3C. Representative voltage clamp recordings in response to hyperpolarizing voltage steps highlight slowly activating inward current. FIG. 3D. Quantification of the sag ratio shown in B) showed no difference by ANOVA ($F(2,19)=2.095$, $p>0.05$) (AAV-eGFP: 1.07±0.01, AAV-N13A: 1.11±0.02, AAV-Δ58: 1.09±0.01, n=9, n=7, n=6). For comparison the sag ratio for AAV-TRIP8b infected neurons is reproduced from FIG. 1. FIG. 3E. Voltage clamp measurements of $I_h$ also showed no difference by ANOVA $F(2,19)=0.09$, $p>0.05$). (AAV-eGFP: 0.24±0.05 pA/pF, AAV-N13A: 0.282±0.09 pA/pF, AAV-Δ58: 0.27±0.04 pA/pF, n=9, 7, 5). For comparison, the $I_h$ amplitude from AAV-TRIP8b infected neurons is reproduced from FIG. 1. All error bars represent±standard error of the mean and are described above as mean±s.e.m.

FIG. 4A, FIG. 4B, FIG. 4C, FIG. 4D, FIG. 4E, FIG. 4F, and FIG. 4G together illustrate that both TRIP8b-HCN binding sites are required for dendritic targeting of HCN channels. FIG. 4A. Confocal images demonstrating that unilateral injection of AAV-N13A causes a reduction in HCN1 staining in the SLM. Top panels show staining for HCN1 (red), middle panel shows staining for eGFP (green), and the bottom panel shows a composite image. Images in the left column are from the uninjected (control) hemisphere, while the right column shows the AAV-N13A injected hemisphere. FIG. 4B and FIG. 4C. Unilateral injection of either AAV-Δ58 or AAV-Δ58/N13A fails to rescue HCN1 distal dendritic enrichment. Display of images is identical to that in A. Scale bar represents 100 μm. FIG. 4D. Quantification of HCN1 distal enrichment. HCN1 staining intensity in regions of interest from the virally injected hemisphere were scaled by staining in the contralateral (uninjected) hemisphere. For comparison, the AAV-TRIP8b rescue experiment is reproduced from FIG. 2. FIG. 4E. Quantification of HCN1 staining in the SLM layer of CA1 (AAV-eGFP=0.98±0.01, AAV Δ58=0.98±0.04, AAV-N13A=0.78±0.04, AAV-Δ58/N13A=0.99±0.07). A one way ANOVA comparing staining intensity in the SLM of the different conditions (AAV-eGFP, AAV-Δ58, AAV-N13A, AAV-Δ58/N13A) was found to be significant ($F(3,17)= 22.375$, $p<0.05$). Tukey's post hoc tests found a difference between AAV-N13A and AAV-eGFP ($p<0.05$), AAV-N13A and AAV-Δ58 ($p<0.05$), and AAV-N13A and AAV-N13A/Δ58 ($p<0.05$). A one way ANOVA comparing HCN1 staining in the cell body layer of the different conditions (AAV-eGFP, AAV-N13A, AAV-Δ58, AAV-Δ58/N13A) was not significant ($F(3,17)=0.59$, $p>0.5$) hence post hoc tests were not performed. FIG. 4F. TRIP8b KO mice bilaterally injected with AAV-N13A, but not AAV-Δ58, show less immobility time on TST and FST. A one way ANOVA examining the immobility time on FST found a significant difference (AAV-eGFP=148.42±18.8 sec, AAV-N13A=40.2±6.7 sec, AAV-Δ58=127.4±25.0 sec, $F(2,18)=67.34$, $P<0.05$), and follow up Tukey's tests revealed a difference between AAV-eGFP and AAV-N13A as well as a difference between AAV-N13A and AAV-Δ58. FIG. 4G. A one way ANOVA examining the immobility time on TST was significantly different (AAV-eGFP=130±12.2 sec, AAV-N13A=44.9±20.1 sec, AAV-Δ58=114±10.0 sec, $F(2, 17)= 62.32$, $p<0.05$) with Tukey's test showing differences between AAV-eGFP and AAV-N13A and between AAV-Δ58 and AAV-N13A. *$p<0.05$ on Tukey's HSD test following one way ANOVA. All error bars represent±standard error of the mean and are described above as mean±s.e.m.

FIG. 7A. Representative immunoblot from hippocampal lysate of TRIP8b KO mice bilaterally injected with AAV-eGFP or AAV-TRIP8b. To ensure that the changes we observed for HCN1 and HCN2 were not the result of neuronal cell death, we also blotted for MAP2 but did not see any differences between the different AAV constructs. All bands appeared near their predicted molecular weights (HCN1 ~105 kDa; HCN2 ~100 kDa; TRIP8b ~70 kDa). FIG. 7B. Densitometry analysis for HCN1. Two tail T test indicated a significant difference between AAV-eGFP (1.01±0.04, n=12) and AAV-TRIP8b(1.44±0.08, n=6, t=4.7, $p<0.001$). FIG. 7C. Densitometry analysis for HCN2. Two tail T test demonstrated a difference between AAV-eGFP (1.00±0.06, n=6) and AAV-TRIP8b (1.76±0.25, n=3, t=3.93, $p<0.01$). All error bars represent±s.e.m. and are described above as mean±s.e.m.

FIG. 9A. Wild Type and TRIP8b KO mice were processed for immunohistochemistry and stained for vesicular GABA transporter (VGAT), an inhibitory presynaptic terminal marker, and HCN1. Note the substantial colocalization of HCN1 at presynaptic terminals in both wild type and TRIP8b KO animals, indicating that loss of TRIP8b does not affect presynaptic HCN1 trafficking. Scale bar represents 40 μm. FIG. 9B. TRIP8b KO mice were unilaterally injected with either AAV-eGFP or AAVTRIP8b and stained for HCN1. In the CA1 cell body layer, we noted no difference in the distribution of HCN1 staining after injection with either AAV-eGFP or AAV-TRIP8b. Scale bar represents 20 μm.

FIG. 10A, FIG. 10B, and FIG. 10C together illustrate that AAV-N13A, AAV-Δ58, and AAV-Δ58/N13A fail to rescue dendritic targeting of HCN2 in TRIP8b KO mice. TRIP8b KO mice were unilaterally injected with AAV-N13A (FIG. 10A), AAV-Δ58 (FIG. 10B), or AAV-Δ58/N13A (FIG. 10C). Display of images is identical to that in FIG. 4. Scale bar represents 100 μm.

FIG. 11A, FIG. 11B, and FIG. 11C together illustrate that AAV-N13A reduces HCN1 and HCN2 protein expression in the hippocampi of TRIP8b KO mice. FIG. 11A. Representative immunoblot from hippocampal lysate of TRIP8b KO mice bilaterally injected with AAV-eGFP, AAV-N13A, AAV-Δ58, or AAV-Δ58/N13A. Western blot bands appeared near their predicted molecular weights (HCN1 ~105 kDa; HCN2 ~100 kDa; TRIP8b ~70 kDa). Note that the Δ58 TRIP8b mutants are lighter than mutant harboring only the N13A mutation, consistent with the loss of 58 amino acids. FIG. 11B. Densitometry analysis for HCN1. A one way ANOVA examining condition (AAV-eGFP, AAV-N13A, AAV-Δ58, AAV-Δ58/N13A) was significant ($F(3,22)=34.2748$, $p<0.05$) with Tukey's test showing differences between AAV-eGFP and AAV-N13A ($p<0.05$), AAV-N13A and AAV-Δ58($p<0.05$), and AAV-Δ58 and AAV-Δ58/N13A ($p<0.05$). FIG. 11C. Densitometry analysis for HCN2. A one way ANOVA comparing HCN2 was significant ($F(3,13)=9.243$, $p<0.05$) with post-hoc tests showing differences between AAV-eGFP and AAV-N13A ($p<0.05$), AAV-Δ58 and AAV-N13A, and AAV-N13A and AAV-Δ58/N13A ($p<0.05$). Finally, we observed no changes in MAP2 for the different TRIP8b constructs indicating that the changes in HCN1 and HCN2 were not a consequence of changes in the number of neurons.

DETAILED DESCRIPTION

Figure 1D:
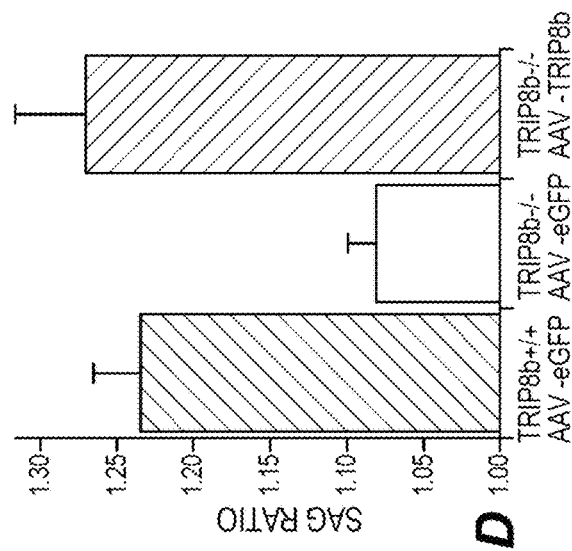

The present invention is described herein using several definitions, as set forth below and throughout the application.

Unless otherwise specified or indicated by context, the terms "a", "an", and "the" mean "one or more." For example, "a therapy" should be interpreted to mean "one or more therapies."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus <10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, the term "subject" may be used interchangeably with the terms "patient" or "individual" and means an animal, which may be a human or non-human animal, in need of treatment. A "subject in need thereof" may include a subject having a disease or disorder associated with an interaction between one or more HCN channels or the subunits thereof and an auxiliary protein or a chaperone protein for the HCN channels or the subunits thereof (e.g., tetratricopeptide repeat (TPR) TRIP8b or a variant thereof). A "subject in need thereof" may include a subject having a neurological disorder. Neurological disorders may include but are not limited to depressive disorders including major depressive disorder (MDD).

TRIP8b

Reference is made herein to TRIP8b and variants thereof and vectors that express TRIP8b or a variant thereof. The amino acid sequence of a C-terminal portion of human (Homo sapiens) TRIP8b is provided herein as SEQ ID NO:1 and variants thereof are provided as SEQ ID NOs:2-5. The amino acid sequence of a C-terminal portion of mouse (Mus musculus) TRIP8b is provided herein as SEQ ID NO:6 and variants thereof are provided as SEQ ID NOs:7-10. An exemplary polypeptide sequence of TRIP8b or a variant thereof for use in the disclosed methods and vectors may comprise the amino acid sequence of any of SEQ ID NOs:1-10, or may comprises an amino acid sequence having at least about 50%, 60%, 70%, 80%, 90%, 95%, 96%, 97%, 98%, or 99% sequence identity to any of SEQ ID NOs:1-10. Variants of TRIP8b may include polypeptides having one or more amino acid substitutions, deletions, additions and/or amino acid insertions relative to a TRIP8b reference polypeptide (e.g., relative to SEQ ID NOs:1-10). Also disclosed are nucleic acid molecules that encode TRIP8b or a variant thereof (e.g., polynucleotides that encode the polypeptide of any of SEQ ID NOs:1-10 or variants thereof).

The disclosed TRIP8b polypeptides or variant polypeptides preferably exhibit one or more biological activities associated with wild-type TRIP8b. For example, the disclosed TRIP8b polypeptides or variant polypeptides may bind to the C-terminal portion of a HCN channel or the C-terminal portion of a subunit of a HCN channel, such as the C-terminal portion of the HCN1, HCN2, HCN3, and/or HCN4 subunit.

As used herein, The terms "amino acid" and "amino acid sequence" refer to an oligopeptide, peptide, polypeptide, or protein sequence (which terms may be used interchangeably), or a fragment of any of these, and to naturally occurring or synthetic molecules. Where "amino acid sequence" is recited to refer to a sequence of a naturally occurring protein molecule, "amino acid sequence" and like terms are not meant to limit the amino acid sequence to the complete native amino acid sequence associated with the recited protein molecule.

The amino acid sequences contemplated herein may include conservative amino acid substitutions and/or non-conservative amino acid substitutions relative to a reference amino acid sequence. For example, a variant TRIP8b polypeptide may include conservative amino acid substitutions and/or non-conservative amino acid substitutions relative to the wild-type TRIP8b polypeptide. "Conservative amino acid substitutions" are those substitutions that are predicted to interfere least with the properties of the reference polypeptide. In other words, conservative amino acid substitutions substantially conserve the structure and the function of the reference protein. The following table provides a list of exemplary conservative amino acid substitutions.

| Original Residue | Conservative Substitution |
| --- | --- |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

In contrast, "Non-conservative amino acid substitutions" are those substitutions that are predicted to interfere most with the properties of the reference polypeptide. For example, non-conservative amino acid substitutions may not conserve the structure and/or the function of the reference protein (e.g., substitution of a polar amino acid for a non-polar amino acid and/or substitution of a negatively charged amino acid for a positively charged amino acid).

A "deletion" refers to a change in the amino acid or nucleotide sequence that results in the absence of one or more amino acid residues or nucleotides relative to a reference sequence (e.g. relative to the amino acid sequence of any of SEQ ID NOs:1-10). A deletion may remove at least 1, 2, 3, 4, 5, 10, 20, 50, 100, or 200 amino acids residues or nucleotides. A deletion may include an internal deletion or a terminal deletion (e.g., an N-terminal truncation and/or a C-terminal truncation of a reference polypeptide or a 5'-terminal and/or 3'-terminal truncation of a reference polynucleotide).

A "fragment" is a portion of an amino acid sequence or a polynucleotide which is identical in sequence to but shorter in length than a reference sequence (e.g. relative to the amino acid sequence of any of SEQ ID NOs:1-10). A fragment may comprise up to the entire length of the reference sequence, minus at least one nucleotide/amino acid residue. For example, a fragment may comprise from 5 to 1000 contiguous nucleotides or contiguous amino acid residues of a reference polynucleotide or reference polypeptide, respectively. In some embodiments, a fragment may comprise at least about 5, 10, 15, 20, 25, 30, 40, 50, 60, 70, 80, 90, 100, 150, 250, or 500 contiguous nucleotides or contiguous amino acid residues of a reference polynucleotide or reference polypeptide, respectively. In some embodiments, a fragment may have a length within a range bounded by any value selected from 5, 10, 15, 20, 25, 30, 40, 50, 60, 70, 80, 90, 100, 150, 250, or 500, contiguous nucleotides or contiguous amino acid residues of a reference polynucleotide or reference polypeptide, respectively. Fragments may be preferentially selected from certain regions of a molecule. The term "at least a fragment" encompasses the full length polynucleotide or full length polypeptide.

A "full length" polynucleotide sequence is one containing at least a translation initiation codon (e.g., methionine) followed by an open reading frame and a translation termination codon. A "full length" polynucleotide sequence encodes a "full length" polypeptide sequence.

In some embodiments, the disclosed polypeptides include variant polypeptides having a non-naturally occurring N-terminal amino acid residue. Unnatural amino acids may include, but are not limited to an amino acid having a D-configuration, an N-methyl-α-amino acid, a non-proteogenic constrained amino acid, or a β-amino acid.

Variant polypeptide may be modified so as to comprise an amino acid sequence, or modified amino acids, or non-naturally occurring amino acids, such that the disclosed variant polypeptides cannot be said to be naturally occurring. In some embodiments, variant polypeptides are modified and the modification is selected from the group consisting of acylation, acetylation, formylation, lipolylation, myristoylation, palmitoylation, alkylation, isoprenylation, prenylation, and amidation. An amino acid in the disclosed polypeptides may be thusly modified, but in particular, the modifications may be present at the N-terminus and/or C-terminus of the polypeptides (e.g., N-terminal acylation or acetylation, and/or C-terminal amidation). The modifications may enhance the stability of the polypeptides and/or make the polypeptides resistant to proteolysis.

"Homology" refers to sequence similarity or, interchangeably, sequence identity, between two or more polynucleotide sequences or two or more polypeptide sequences. Homology, sequence similarity, and percentage sequence identity may be determined using methods in the art and described herein.

The phrases "percent identity" and "% identity," for example, as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases.

Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

A "variant" of a particular polypeptide sequence is defined as a polypeptide sequence having at least 50% sequence identity to the particular polypeptide sequence over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of polypeptides may show, for example, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides. A "variant" may have substantially the same functional activity as a reference polypeptide. For example, a variant of TRIP8b may bind to the C-terminal portion of a HCN channel or the C-terminal portion of a subunit of a HCN channel, such as the C-terminal portion of the HCN1, HCN2, HCN3, and/or HCN4 subunit.

Gene Therapy and Vectors for Expressing TRIP8b

In some embodiments of the disclosed methods, a subject in need thereof may be administered gene therapy in order to express a heterologous DNA, such as DNA encoding TRIP8b or a variant thereof, in order to treat a neurological disorder such as major depressive disorder (MDD). In some embodiments of the disclosed methods, a subject in need thereof is administered a vector, which may be a viral vector or non-viral vector in order to express a heterologous DNA, such as DNA encoding TRIP8b or a variant thereof, in order to treat a neurological disorder such as major depressive disorder (MDD). Gene therapy and vectors, including viral and non-viral vectors for gene transfer or expression, RNAi, and CRISPR/Cas9 genome editing for therapeutic purposes are known in the art. (See, e.g., Keeler et al., "Gene Therapy 2017: Progress and Future Directions," Clin Transl Sci. 2017 July; 10(4):242-248; Dunbar et al., "Gene therapy comes of age," Science, 12 Jan. 2018: Vol. 359, Issue 6372; Kumar et al., "Clinical development of gene therapy: results and lessons from recent successes," Molecular Therapy—Methods & Clinical Development (2016) 3, 16034; the contents of which are incorporated herein by reference in their entireties).

In some embodiments of the disclosed methods, a subject in need therefore is administered a vector in order to express a heterologous DNA, such as DNA encoding TRIP8b or a variant thereof, in order to treat a neurological disorder such as major depressive disorder (MDD). In the disclosed methods, any conventional vectors may be used for expressing TRIP8b or a variant thereof in a subject in need thereof. The term "vector" refers to some means by which heterologous DNA, such as DNA encoding TRIP8b or a variant thereof, can be introduced and expressed in a cell or cells forming a tissue. There are various types of vectors suitable for the disclosed methods, and suitable vectors may include viral vectors. As used herein, a "viral vector" (e.g., an adenovirus or adeno-associated virus, Sendai virus, or measles virus vector) refers to recombinant viral nucleic acid that has been engineered to express a heterologous polypeptide (e.g., TRIP8b polypeptide or a variant thereof). The recombinant viral nucleic acid typically includes cis-acting elements for expression of the encoded heterologous polypeptide (e.g., a polypeptide comprising the amino acid sequence of any of SEQ ID NOs:1-10). The recombinant viral nucleic acid typically is capable of being packaged into a helper virus that is capable of infecting a host cell. For example, the recombinant viral nucleic acid may include cis-acting elements for packaging. Typically, the viral vector is not replication competent or is attenuated. An "attenuated recombinant virus" refers to a virus that has been genetically altered by modern molecular biological methods (e.g., restriction endonuclease and ligase treatment, and rendered less virulent than wild type), typically by deletion of specific genes. For example, the recombinant viral nucleic acid may lack a gene essential for the efficient production or essential for the production of infectious virus. The recombinant viral nucleic acid, packaged in a virus (e.g., a helper virus) may be introduced into a human subject by standard methods.

Numerous virus species can be used as the recombinant virus vectors for the pharmaceutical composition disclosed herein. A preferred recombinant virus is adeno-associated virus. Adeno-associated viral (AAV) vectors are recognized as an emerging gene therapy platform for the treatment of neurological diseases. (See, e.g., Deverman et al., "Gene therapy for neurological disorders: progress and prospects," Nature Reviews Drug Discovery," 17 641-659 (2018), the content of which is incorporated herein by reference in its entirety). Others include adenoviruses, retroviruses that are packaged in cells with amphotropic host range, vaccinia virus, canarypox, Sendai virus, measles virus, Yellow Fever vaccine virus (e.g., 17-D or similar), attenuated or defective DNA viruses, such as but not limited to herpes simplex virus (HSV), papillomavirus, and Epstein Barr virus (EBV).

Methods and Compositions for Treating Neurological Disorders and Identifying Therapeutic Agents for Treating Neurological Disorders Disclosed are methods and compositions for treating a subject having a neurological disorder, which may include but is not limited to depressive disorders such as major depressive disorder (MDD). The methods and compositions may be utilized in order to inhibit trafficking of hyperpolarization-activated cyclic nucleotide gated (HCN) channels or subunits thereof.

The HCN channels of the disclosed methods may comprise, for example, HCN1 subunits, HCN2 subunits, or a combination thereof, and also may comprise, for example, HCN3 subunits, HCN4 subunits, or a combination thereof. In some embodiments of the disclosed methods, trafficking of the HCN channels or subunits thereof results in inhibiting distal dendritic enrichment of HCN1 and HCN2 in pyramidal neurons of hippocampal area CA1.

In the disclosed methods, the trafficking of HCN channels or the subunits thereof may be inhibited by a number of suitable means. In some embodiments, inhibition of trafficking of HCN channels or the subunits thereof is achieved by administering to a subject having a neurological disorder a vector that expresses an auxiliary protein or chaperone protein for the HCN channels or the subunits thereof. Suitable auxiliary proteins or chaperone proteins may include, but are not limited to tetratricopeptide repeat (TPR)-containing Rab8b interacting (TRIP8b) protein (SEQ ID NO:1 or 6) or a variant thereof (SEQ ID NOs:2-5 and 7-10). Variants of TRIP8b that may be utilized in the disclosed methods and/or that may be utilized in the disclosed vectors may include variants disclosed in the art. (See e.g., Han et al., "Trafficking and Gating of Hyperpolarization-activated Cyclic Nucleotide-gated Channels Are Regulated by Interaction with Tetratricopeptide Repeat-containing Rab8b-interacting Protein (TRIP8b) and Cyclic AMP at Distinct Sites," J. Biol. Chem., Jun. 10, 2011, Volume 286, Number 23, pages 20823-20834, the content of which is incorporated herein by reference in its entirety).

In some embodiments of the disclosed methods and the vectors utilized in the disclosed methods, variants of TRIP8b may include variants having a mutation in the tetratricopeptide repeat (TPR) that disrupts binding of the TPR with the C-terminus of the HCN channel or subunits thereof, for example, where the mutation is a substitution of alanine for asparagine at the $13^{th}$ amino acid in the third TPR domain (TPR3-N13A) (SEQ ID NOs:2 and 7), the mutation is a substitution of lysine for glutamic acid at the $15^{th}$ amino acid in the second TPR domain (TPR2-E15K) (SEQ ID NOs:3 and 8), the mutation is a substitution of alanine for asparagine at the $5^{th}$ amino acid in the fifth TPR domain (TPR5-N5A) (SEQ ID NOs:4 and 9), and the mutation is a substitution of alanine for arginine at the $2^{nd}$ amino acid in the sixth TPR domain (TPR6-R2A) (SEQ ID NOs:5 and 10).

Suitable vectors for the disclosed methods may include viral vectors. Suitable viral vectors may include but are not limited to adeno-associated viral vector (AAV). As such, also disclosed herein are viral vectors that express auxiliary proteins or chaperone proteins such as TRIP8b protein or a variant thereof. For example, the disclosed viral vectors may express a variant of TRIP8b having a mutation in the tetratricopeptide repeat (TPR) that disrupts binding of the TPR with the C-terminus of the HCN channel or subunits thereof (e.g., where the mutation is a substitution of alanine for asparagine at the $13^{th}$ amino acid (N13A) in the third TPR domain). Viral vectors have been used to express TRIP8b in animal models of depression and rescue $I_h$, a cationic current that regulates neuronal excitability. (See Han et al., "HCN channel dendritic targeting requires bipartite interaction with TRIP8b and regulates antidepressant-like behavioral effects," Mol Psychiatry 2017 March; 22(3): 458-465; the content of which is incorporated herein by reference in its entirety).

Also contemplated herein is the use of so-called "small molecule compounds" as inhibitors of trafficking of HCN channels or subunits thereof. As such, the methods disclosed herein include treating a subject having a neurological disorder by inhibiting the trafficking of HCN channels or subunits thereof by administering a compound that inhibits an interaction between the HCN channels or the subunits thereof and an auxiliary protein or a chaperone protein for the HCN channels or the subunits thereof. For example, the small molecule compound may inhibit and interaction between HCN1 or HCN2 and TRIP8b. In particular, the small molecule compound may inhibit binding of a tetratricopeptide repeat (TPR) TRIP8b and the C-terminus of the HCN channel or HCN1 or HCN2 subunits thereof.

Also contemplated herein are screening methods, for example, screening methods for identifying an inhibitor of an interaction between the HCN channels or the subunits thereof and an auxiliary protein or a chaperone protein for the HCN channels or the subunits thereof (e.g., tetratricopeptide repeat (TPR) TRIP8b or a variant thereof). The screening methods may include steps of: (a) reacting: (i) a test compound (e.g., a so-called small molecule), (ii) one or more of the HCN channels or the subunits thereof (optionally where the HCN channels or the subunits thereof are labeled with a fluorophore), and (iii) the auxiliary protein or the chaperone protein for the HCN channels or the subunits thereof (optionally where the auxiliary protein or the chaperone protein for the HCN channels or the subunits thereof is labeled with a fluorophore), and (b) detecting inhibition by the test compound of the interaction between the HCN channels or the subunits thereof and the auxiliary protein or a chaperone protein for the HCN channels or the subunits thereof (e.g., by performing a Fluorescence Polarization (FP)-based assay). A screening method as contemplated herein is described in Han et al., "Method for Identifying Small Molecule Inhibitors of the Protein-protein Interaction Between HCN1 and TRIP8b," J. Vis. Exp. 2016 Nov. 11; (117), the content of which is incorporated herein by reference in its entirety. In Han et al., an expanded description of a method for purifying TRIP8b and executing a high throughput screen to identify small molecule inhibitors of the interaction between HCN and TRIP8b, is described. The method for high throughput screening utilizes a Fluorescence Polarization (FP)-based assay to monitor the binding of a large TRIP8b fragment to a fluorophore-tagged eleven amino acid peptide corresponding to the HCN1 C-terminal tail. This method allows "hit" compounds to be identified based on the change in the polarization of emitted light. Validation assays are then performed to ensure that "hit" compounds are not artifactual.

A screening method as contemplated herein also is disclosed in Han et al., "Identification of small molecule inhibitors of hyperpolarization-activated cyclic nucleotide gated channels," J. Biol. Screen. 2015 October; 20(9): 1124-1131, the content of which is incorporated herein by reference in its entirety. To target the function of the HCN channel in the brain without affecting channels' function in the heart, Han et al. proposed disrupting the interaction between HCN and TRIP8b and developed a high throughput fluorescence polarization (FP) assay to identify small molecules capable of disrupting this interaction. Han et al. used this FP assay to screen a 20,000-compound library and identified a number of active compounds. The active compounds were validated using an orthogonal AlphaScreen assay to identify one compound (0.005%) as the first confirmed hit for inhibiting the HCN-TRIP8b interaction. Identifying small molecules capable of disrupting the interaction between HCN and TRIP8b should enable the development of new research tools and small molecule therapies that could benefit patients with depression.

Small molecule inhibitors identified by the screening methods may be formulated as pharmaceutical compositions for treating neurological diseases and disorders as contemplated herein. For example, small molecule inhibitors identified by the screening methods may be formulated as pharmaceutical compositions for treating major depressive disorder (MDD).

The disclosed compositions and methods may be utilized and/or practiced using animal models Animal models for major depressive disorder (MDD) have been described. (For a Review, see Lyman et al., "Animal models suggest the TRIP8b-HCN interaction is a therapeutic target for major depressive disorder," Exp. Opin. Thera. Targets, 2017, Vol. 21, No. 3, 235-237, the content of which is incorporated herein by reference in its entirety.

Illustrative Embodiments

The following embodiments are illustrative and should not be interpreted to limit the scope of the claimed subject matter.

Embodiment 1. A method for treating a subject having a neurological disorder, optionally where the neurological disorder is major depressive disorder (MDD), the method comprising inhibiting the trafficking of hyperpolarization-activated cyclic nucleotide gated (HCN) channels or subunits thereof.

Embodiment 2. The method of embodiment 1, wherein the HCN channels comprise HCN1 subunits, HCN2 subunits, or a combination thereof.

Embodiment 3. The method of embodiment 1 or 2, wherein inhibiting the trafficking of hyperpolarization-activated cyclic nucleotide gated (HCN) channels or subunits thereof inhibits distal dendritic enrichment of HCN1 and HCN2 in pyramidal neurons of hippocampal area 1 (CA1).

Embodiment 4. The method of any of the foregoing embodiments, wherein inhibiting the trafficking of hyperpolarization-activated cyclic nucleotide gated (HCN) channels comprises administering to the subject a vector that expresses an auxiliary protein or a chaperone protein for the HCN channels or the subunits thereof.

Embodiment 5. The method of embodiment 4, wherein the auxiliary protein or the chaperone protein comprises tetratricopeptide repeat (TPR)-containing Rab8b interacting (TRIP8b) protein or a variant thereof.

Embodiment 6. The method of embodiment 4 or 5, wherein the auxiliary protein or the chaperone protein is a variant of TRIP8b having a mutation in the tetracopeptide repeat (TPR) that disrupts binding of the TPR with the C-terminus of the HCN channel or subunits thereof.

Embodiment 7. The method of embodiment 6, wherein the mutation is selected from the group consisting of a substitution of alanine for asparagine at the $13^{th}$ amino acid in the third TPR domain (TPR3-N13A), a substitution of lysine for glutamic acid at the $15^{th}$ amino acid in the second TPR domain (TPR2-E15K), a substitution of alanine for asparagine at the $5^{th}$ amino acid in the fifth TPR domain (TPR5-N5A), a substitution of alanine for arginine at the $2^{nd}$ amino acid in the sixth TPR domain (TPR6-R2A), and any combination thereof.

Embodiment 8. The method of any of embodiments 4-7, wherein the vector is an adeno-associated viral vector.

Embodiment 9. The method of any of embodiments 1-3, wherein inhibiting the trafficking of hyperpolarization-activated cyclic nucleotide gated (HCN) channels comprises administering to the subject a pharmaceutical composition that comprises an inhibitor of an interaction between the auxiliary protein or the chaperone protein and the HCN channels or the subunits thereof.

Embodiment 10. A viral vector that expresses TRIP8b protein or a variant thereof, optionally, wherein the auxiliary protein or the chaperone protein is a variant of TRIP8b having a mutation in the tetratricopeptide repeat (TPR) that disrupts binding of the TPR with the C-terminus of the HCN channel or subunits thereof.

Embodiment 11. The viral vector of embodiment 10, wherein the mutation is selected from the group consisting of a substitution of alanine for asparagine at the $13^{th}$ amino acid in the third TPR domain (TPR3-N13A), a substitution of lysine for glutamic acid at the $15^{th}$ amino acid in the second TPR domain (TPR2-E15K), a substitution of alanine for asparagine at the $5^{th}$ amino acid in the fifth TPR domain (TPR5-N5A), a substitution of alanine for arginine at the $2^{d}$ amino acid in the sixth TPR domain (TPR6-R2A), and any combination thereof.

Embodiment 12. A variant of TRIP8b having a mutation in the tetratricopeptide repeat (TPR) that disrupts binding of the TPR with the C-terminus of the HCN channel or subunits thereof.

Embodiment 13. The variant of embodiment 12, wherein the mutation is selected from the group consisting of a substitution of alanine for asparagine at the $13^{th}$ amino acid in the third TPR domain (TPR3-N13A), a substitution of lysine for glutamic acid at the $15^{th}$ amino acid in the second TPR domain (TPR2-E15K), a substitution of alanine for asparagine at the $5^{th}$ amino acid in the fifth TPR domain (TPR5-N5A), a substitution of alanine for arginine at the $2^{nd}$ amino acid in the sixth TPR domain (TPR6-R2A), and any combination thereof.

Embodiment 14. A pharmaceutical composition comprising the variant of embodiment 12 or 13 together with a suitable pharmaceutical carrier.

Embodiment 15. A screening method for identifying an inhibitor of an interaction between the HCN channels or the subunits thereof and an auxiliary protein or a chaperone protein for the HCN channels or the subunits thereof, the method comprising: (a) reacting: (i) a test compound, (ii) the HCN channels or the subunits thereof, and (iii) the auxiliary protein or a chaperone protein for the HCN channels or the subunits thereof, and (b) detecting inhibition by the test compound of the interaction between the HCN channels or the subunits thereof and the auxiliary protein or a chaperone protein for the HCN channels or the subunits thereof.

Embodiment 16. A method for treating a subject having a neurological disorder, the method comprising inhibiting the trafficking of hyperpolarization-activated cyclic nucleotide gated (HCN) channels or subunits thereof by administering a compound that inhibits an interaction between the HCN channels or the subunits thereof and an auxiliary protein or a chaperone protein for the HCN channels or the subunits thereof.

Embodiment 17. The method of embodiment 16, wherein the neurological disorder is major depressive disorder (MDD).

Embodiment 18. The method of embodiment 16 or 17, wherein the HCN channels comprise HCN1 subunits, HCN2 subunits, or a combination thereof.

Embodiment 19. The method of any of embodiments 16-18, wherein inhibiting the trafficking of hyperpolarization-activated cyclic nucleotide gated (HCN) channels or subunits thereof inhibits distal dendritic enrichment of HCN1 and HCN2 in pyramidal neurons of hippocampal area CA1.

Embodiment 20. The method of any of embodiments 16-19, wherein the auxiliary protein or the chaperone protein comprises tetratricopeptide repeat (TPR)-containing Rab8b interacting (TRIP8b) protein or a variant thereof.

EXAMPLES

The following Examples are illustrative and are not intended to limit the scope of the claimed subject matter.

Example 1

HCN-Channel Dendritic Targeting Requires Bipartite Interaction with TRIP8b and Regulates Antidepressant-Like Behavioral Effects Reference is made to the manuscript entitled, "HCN Channel Dendritic Targeting Requires Bipartite Interaction with TRIP8b and Regulates Antidepressant-like Behavioral Effects," by Ye Han et al., Mol. Psychiatry, 2017, March; 22(3):458-465, the content of which is incorporated by reference in this application in its entirety.

Abstract

Major Depressive Disorder is a prevalent psychiatric condition with limited therapeutic options beyond monoaminergic therapies. Although effective in some individuals, many patients fail to respond adequately to existing treatments and new pharmacologic targets are needed. HCN channels regulate excitability in neurons and blocking HCN channel function has been proposed as a novel antidepressant strategy. However, systemic blockade of HCN channels produces cardiac effects that limit this approach. Knockout (KO) of the brain-specific HCN channel auxiliary subunit TRIP8b also produces antidepressant-like behavioral effects and suggests that inhibiting TRIP8b function could produce antidepressant-like effects without affecting the heart. We examined the structural basis of TRIP8b-mediated HCN channel trafficking and its relationship to antidepressant-like behavior using a viral rescue approach in TRIP8b KO mice. We found that restoring TRIP8b to the hippocampus was sufficient to reverse the impaired HCN channel trafficking and antidepressant-like behavioral effects caused by TRIP8b KO. Moreover, we found that hippocampal expression of a mutated version of TRIP8b further impaired HCN channel trafficking and increased the antidepressant-like behavioral phenotype of TRIP8b KO mice. Thus, modulating the TRIP8b-HCN interaction bidirectionally influences channel trafficking and antidepressant-like behavior. Overall, our work suggests that small molecule inhibitors of the interaction between TRIP8b and HCN should produce antidepressant-like behaviors and could represent a new paradigm for the treatment of Major Depressive Disorder.

Introduction

Major Depressive Disorder (MDD) is a common mental illness that causes tremendous health and social issues worldwide[1, 2]. Pharmacological treatment of MDD consists primarily of drugs targeting monoaminergic neurotransmitters, but there is a need for additional therapeutic options because many patients fail to respond to these therapies. Recent evidence suggests that changes in excitability within neural circuits of the hippocampus may play an important role in MDD[3-5]. These findings raise the possibility that therapies affecting cellular excitability could function as novel antidepressants[6, 7].

Hyperpolarization-activated cyclic nucleotide-gated (HCN) channels are encoded by four pore-forming subunits (HCN1-4) and mediate $I_h$, a cationic current that regulates neuronal excitability[8, 9]. In pyramidal neurons of hippocampal area CA1, HCN channels are enriched in distal dendrites where they reduce network excitability by limiting integration of synaptic inputs and dampening $Ca^{2+}$ signaling[10-12]. This unique subcellular distribution of HCN channels is regulated by Tetratricopeptide repeat-containing Rab8b interacting protein (TRIP8b), an auxiliary subunit of HCN channels expressed uniquely in the nervous system[13-16]. Loss of TRIP8b eliminates the distal dendritic enrichment of HCN channels in pyramidal neurons of CA1 and leads to increased hippocampal excitability[16]. Knockdown of HCN1 in CA1[17] and genetic ablation of HCN1, HCN2, or TRIP8b[16] all produce an increase in neuronal excitability and, interestingly, all lead to antidepressant-like effects on behavior. Although these results suggest that blocking HCN channels could be useful in treating MDD, the important role of $I_h$ in cardiac function limits the clinical utility of systemic pharmacological blockade. Because TRIP8b is not expressed in the heart, we reasoned that disrupting the interaction between TRIP8b and HCN could increase hippocampal excitability and produce antidepressant-like behavioral effects without affecting HCN channels in the heart. In this paper, we establish the importance of the interaction between TRIP8b and HCN channels for channel trafficking and antidepressant-like behavioral effects.

TRIP8b binds to HCN pore-forming subunits at two distinct sites[18, 19]. While both sites independently influence subcellular trafficking in heterologous expression systems[18, 19], it is less clear how the distinct interactions affect channel function and behavior in the brain. To define the importance of the two TRIP8b-HCN interactions in vivo, we used adeno-associated viral (AAV) vectors to express wild type and mutant TRIP8b in the hippocampus of TRIP8b knockout (KO) mice. We found that restoring TRIP8b expression in CA1 neurons is sufficient to rescue the enrichment of HCN channels in CA1 pyramidal neuron distal dendrites and reverse the antidepressant-like behavior of TRIP8b KO mice. Mutating either interaction site prevented TRIP8b-mediated restoration of channel trafficking and reversal of antidepressant-like behavior. However, a mutant TRIP8b construct lacking the ability to interact with the HCN channel at its C-terminal tail further reduced the expression of HCN channels in dendrites of TRIP8b KO mice and increased their antidepressant-like behavior. These experiments demonstrate that disrupting either TRIP8b-HCN binding site interferes with HCN channel trafficking and function. Overall, our data suggest that disrupting the protein-protein interactions between TRIP8b and HCN channel pore-forming subunits should produce antidepressant-like behavioral effects and that targeting the interaction between TRIP8b and the HCN channel C-terminal tail may be particularly effective as a potential new therapeutic approach for MDD.

Materials and Methods

Mice. All animal experiments were performed according to protocols approved by the Institutional Animal Care and Use Committees of Northwestern University.

Viral injections. Commercially generated AAV (Penn Vector) were prepared using custom plasmids and injected into the CA1 cell body layer of mice under stereotaxic control. AAV2/8 serotype was chosen to ensure high expression levels in the CA1 with minimal inflammation[20].

Generation of global TRIP8b knockout mice used in this study has been previously described[16]. Wild type C57Bl/6 mice were obtained from Jackson Laboratories. Mice (age 4-6 weeks) were anesthetized with an intraperitoneal injection of ketamine (100 mg/kg) and xylazine (10 mg/kg) and mounted on a stereotaxic instrument (Stoelting, Wood Dale, Ill.). A small incision was made to expose the skull and a small craniotomy made with a dental drill. 1 µl of 3×1012 vector genome (vg)/ml of AAV was injected into the dorsal hippocampus of TRIP8b KO mice at a rate of 0.3 µl/min via a 5 µl Hamilton syringe. The injection co-ordinates were 2.3 mm A/P, ±1.3 mm MIL, −1.7 mm DIV. The needle was slowly removed at a rate of 1 mm min−1 following holding in the injection site for 5 min to allow for diffusion of the virus.

Immunohistochemistry and Electrophysiology. Experiments were performed as described elsewhere.[21] Mice were deeply anesthetized with isoflurane and transcardially perfused with cold PBS followed by 4% paraformaldehyde. Brains were then removed and post-fixed in 4% PFA overnight. 30 µm coronal sections were made on a vibratome (Leica, Buffalo Grove, Ill.). Antigen retrieval was performed with 10 mM Na-citrate, pH 9.0, for 10 minutes at 80° C.

prior to blocking in PBS with 5% normal goat serum and 0.03% Triton X-100 for 1 hour. Primary antibodies were diluted in blocking solution and applied overnight at 4° C. Sections were washed 3 times prior to a 1 hour incubation at room temperature in secondary antibody, followed by 3 additional washes in PBS. DAPI was included in the final wash and tissue was then mounted on glass slides with PermaFluor (Thermo Fisher Scientific, Fremont, Calif.). Imaging was performed at the Northwestern University Center for Advanced Microscopy on a Nikon A1R confocal microscope using MS Elements software (Nikon, Melville, N.J.) and TissueGnostics, and analyzed using FIJI. Primary antibodies used were custom guinea pig anti-HCN1, guinea pig anti-HCN2, and rabbit anti-TRIP8b2, and rabbit anti-GFP (Millipore, Temecular, Calif.). The sensitivity and specificity of these antibodies have been verified extensively in previous reports4-6. All secondary antibodies were purchased from Invitrogen. For quantification of images (FIG. 2 and FIG. 4), custom written routines in MATLAB (Mathworks, Natick, Mass.) were used. Regions of interest (ROI) were drawn over the stratum oriens and stratum pyramidale. A large ROI was also drawn over the region encompassing the stratum radiatum and stratum lacunosum moleculare and then subdivided into ten equally spaced ROIs. The mean intensity of the staining within each ROI was then used for subsequent downstream analyses. Within each slice, the staining intensity of the injected hemisphere was divided by the intensity of the staining in the corresponding ROI from the contralateral hemisphere.

Western blotting. Western blotting was performed as previously described2. Primary antibodies used were: custom rabbit anti-HCN1, rabbit anti-HCN2 and guinea pig anti-TRIP8b2, rabbit anti-MAP2 (Millipore Temecular, Calif.); and mouse anti-tubulin (Millipore Temecular, Calif.). Primary antibodies were diluted in blocking solution containing 5% milk and 0.1% Tween-20 in TBS (TBS-T). Band intensities were quantified using MH ImageJ software and normalized to the anti-tubulin signalfor each sample.

Electrophysiology. Mice were deeply anesthetized with isoflurane, decapitated, and the whole brain was rapidly dissected into ice-cold sucrose solution containing (in mM): 190 sucrose, 10 NaCl, 2.5 KCl, 25 NaHCO3, 1.25 NaH2PO4, 0.5 CaCl2, 7 MgCl2, 25 dextrose; pH 7.4. All solutions were continuously bubbled with 95% O2/5% CO2. 300 μm sagittal slices were made using a vibratome (Leica) and immediately transferred to a 35° C. holding chamber containing ACSF (125 NaCl, 2.5 KCl, 25 NaHCO3, 1.25 NaH2PO4, 2 CaCl2, 1 MgCl2, 25 dextrose; pH 7.4). After a 25-minute incubation period, the chamber was allowed to equilibrate to room temperature for ≥30 minutes before use. For recording, slices were transferred to a custom chamber perfused with room temperature (22±1° C.), oxygenated ACSF at 1-2 mL/min. Electrodes (4-6 MS2) were pulled on a Sutter P87 pipette puller and filled with intracellular solution containing: 115 K-gluconate, 20 KCl, 10 HEPES, 10 Na-phosphocreatine, 2 Mg-ATP, 0.3 Na-GTP, 0.2% biocytin. KOH was added to pH 7.3. Whole-cell recordings were made with a PC-ONE amplifier (Dagan), filtered at 3 kHz, and digitized at 20 kHz using an InstruTECH ITC16. A calculated liquid junction potential of 13 mV was compensated prior to approaching each cell. Series resistance was monitored throughout each experiment, and cells were discarded if the series resistance exceeded 30 MΩ. Data acquisition and analysis was performed in IgorPro 6 (Wave-Metrics) using custom macros. Ih density at −130 mV was obtained by subtracting the instantaneous current after the capacitive transient from the steady-state current at the end of a 2 s step.

Plasmid constructs. All restriction enzymes were purchased from New England Biolabs (NEB). All oligonucleotides for use in PCR amplification and oligo insertion were synthesized by Integrated DNA Technologies (IDT). All plasmids were verified by DNA sequencing (Northwestern Sequencing Core).

Description of Virus Production. The DNA plasmid for pAAV-hsynapsin-Cre-IRES-eGFP was kindly provided by Dr. Pavel Osten (Cold Spring Harbor Laboratory). pAAV-hsynapsin-IRES-eGFP was generated by excising Cre using EcoRI followed by insertion of restriction sites using selected oligonucleotides. pAAV-hsynapsin-TRIP8b (1a-4)-IRES-eGFP (pAAV-1a-4) was generated by EcoRI/XbaI digestion of pXEGFP-TRIP8b(1a-4)[16] followed by blunt ligation and insertion into pAAV-hsynapsin-IRES-eGFP, which was digested by EcoRV. pAAVN13A was generated by EcoRV/Bsu361 digestion of pXEGFP-TRIP8b(1a-4) (TPR3-N13A)[19] followed by subcloning into pAAV-1a-4 at EcoRV/Bsu361 sites. pAAV-Δ58 was generated by SpeI/BamHI digestion of pXEGFP-TRIP8b (1a-4)(Δ58) followed by subcloning into pAAV-1a-4 at SpeI/BamI sites[19]. AAV serotype 2/8 vectors were produced by the Gene Therapy Program of the University of Pennsylvania.

Results

Figure 1F:
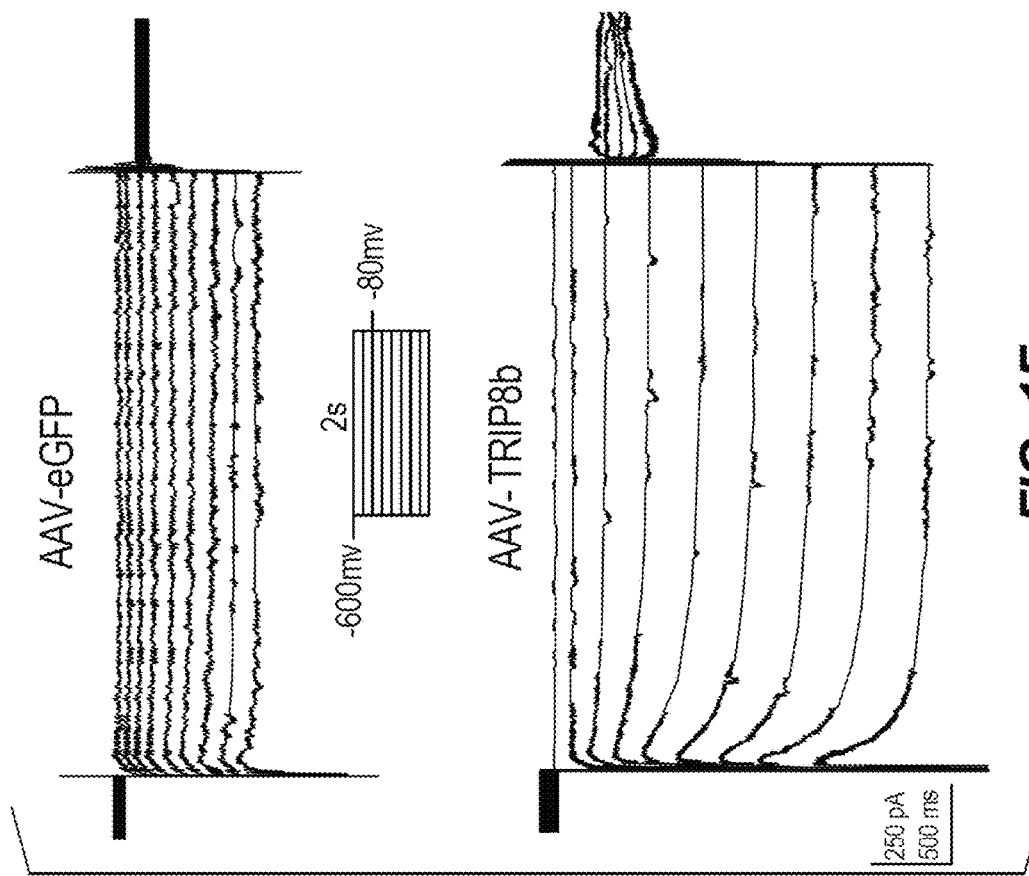
FIG. 1F. Voltage clamp traces from eGFP positive cells in TRIP8b KO mice show a slowly activating inward current in response to hyperpolarizing voltage steps after infection with AAV-TRIP8b. All error bars represent±standard error of the mean and are described above as mean±s.e.m. *p<0.05 on Tukey's test following one way ANOVA.
Figure 1E:
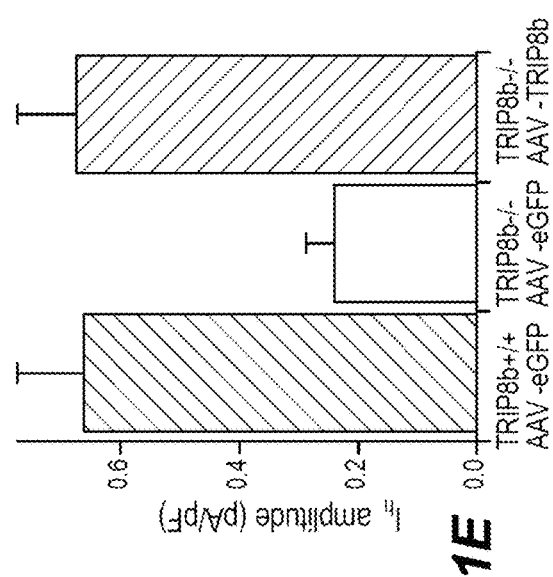
Figure 5:
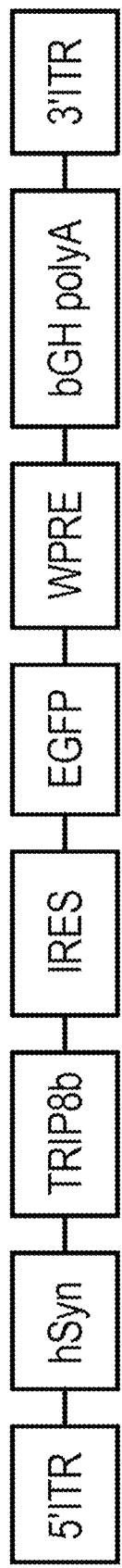
FIG. 5 illustrates a schematic of AAV-TRIP8b constructs. The expression of TRIP8b was driven by human synapsin (hSyn) promoter and enhanced by woodchuck hepatitis virus post-transcriptional regulatory element (WPRE). ITR, inverted terminal repeat; IRES, internal ribosome entry site; bGH polyA, bovine growth hormone polyadenylation.

Viral expression of TRIP8b rescues $I_h$ in CA1 pyramidal neurons of TRIP8b KO mice. TRIP8b KO mice lack all TRIP8b isoforms and have a reduction in both the distal dendritic enrichment of HCN channels and somatic $I_h$ in CA1 pyramidal neurons[16]. Although TRIP8b has many splice isoforms, previous work has shown that an isoform comprised of exons 1a, 4, and exons 5-16 (TRIP8b(1a-4)) is the most common[13, 22]. Thus we began by determining if this isoform is sufficient to rescue HCN channel distal dendritic enrichment. We generated an AAV carrying TRIP8b (FIG. 1A, AAV-TRIP8b-IRES-eGFP, hereafter referred to as AAV-TRIP8b) driven by the human synapsin promoter in order to restrict expression to neurons. (See FIG. 5). To investigate if AAV-TRIP8b rescues somatic $I_h$, we bilaterally injected the CA1 of TRIP8b KO mice with AAV-eGFP or AAV-TRIP8b and injected wild type (WT) mice with AAV-eGFP as a positive control. We then made whole-cell recordings from the eGFP-labeled CA1 pyramidal neurons. As expected, AAV-eGFP did not influence $I_h$ in wild type or TRIP8b KO pyramidal neurons. WT pyramidal neurons infected with control AAV-eGFP displayed a current characteristic of $I_h$ that is noticeably reduced in TRIP8b KO mice infected with AAV-eGFP. TRIP8b KO mice infected with AAV-TRIP8b showed rescue of the sag ratio (FIG. 1C and FIG. 1D, measured as $\Delta V_{max}/\Delta V_{steady-state}$). Voltage clamp measurements of $I_h$ produced similar results (FIG. 1E and FIG. 1F). Expression of AAV-TRIP8b in TRIP8b KO mice yielded large, slowly activating inward currents in response to hyperpolarizing voltage steps that were significantly larger than currents recorded from AAV-eGFP control neurons. No change in resting membrane potential or resistance was noted. (Table 1).

TABLE 1

| Genotype | Virus | Membrane Resistance, MΩ | Resting Membrane Potential, mV | Half Activation Potential, mV | Time Constant, ms |
| --- | --- | --- | --- | --- | --- |
| TRIP8b KO | AAV-eGFP | 376.8 (87.3, 9) | −67.4 (2.9, 9) | −99.55 (4.3, 7) | 250 (28, 7) |
| TRIP8b KO | AAV-TRIP8b | 196.2 (48.9, 8) | −69.4 (3.8, 8) | −90 (3.5, 7) | 186 4, 7) |

Table 1 provides a summary of membrane properties from CA1 pyramidal neurons infected with AAV-eGFP or AAV-TRIP8b. Table 1 lists the genotype of the animal used for the experiment, the virus injected, and then the membrane resistance and resting membrane potential. Half activation potential was determined in voltage clamp by holding the cells at −60 mV and then stepping the cell to progressively more hyperpolarized potentials. The time constant is the result of a monoexponential fit of channel activation when stepping from a holding potential of −60 mV to −120 mV. Two tail T tests were not significant when comparing membrane resistance, resting membrane potential, half activation potential, or time constant (p>0.05 in all cases). Data presented as mean (s.e.m., n).

Figure 2A:
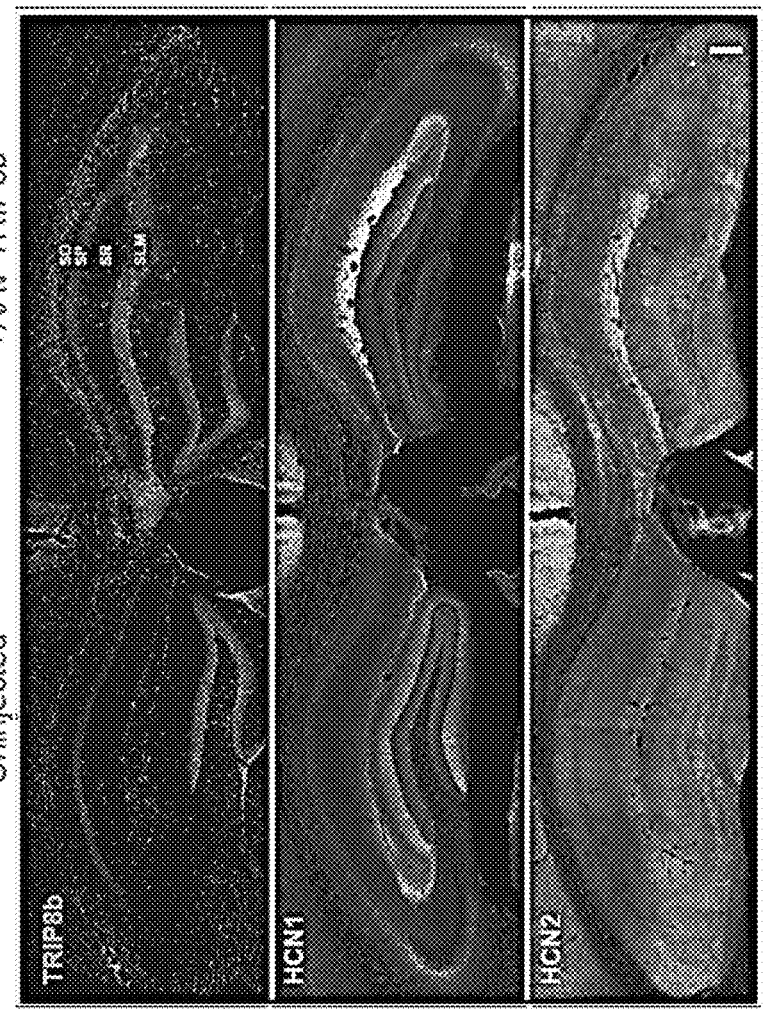
FIG. 2A, FIG. 2B, FIG. 2C, and FIG. 2D together illustrate that dendritic targeting of HCN channels is rescued by viral delivery of TRIP8b.
Figure 2B:
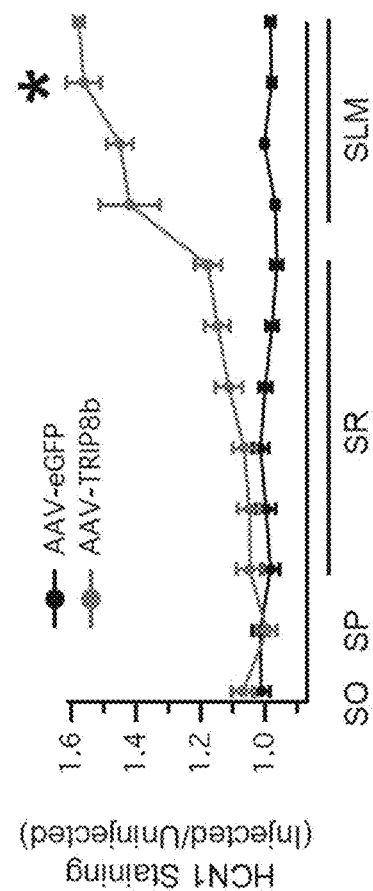
Figure 6B:
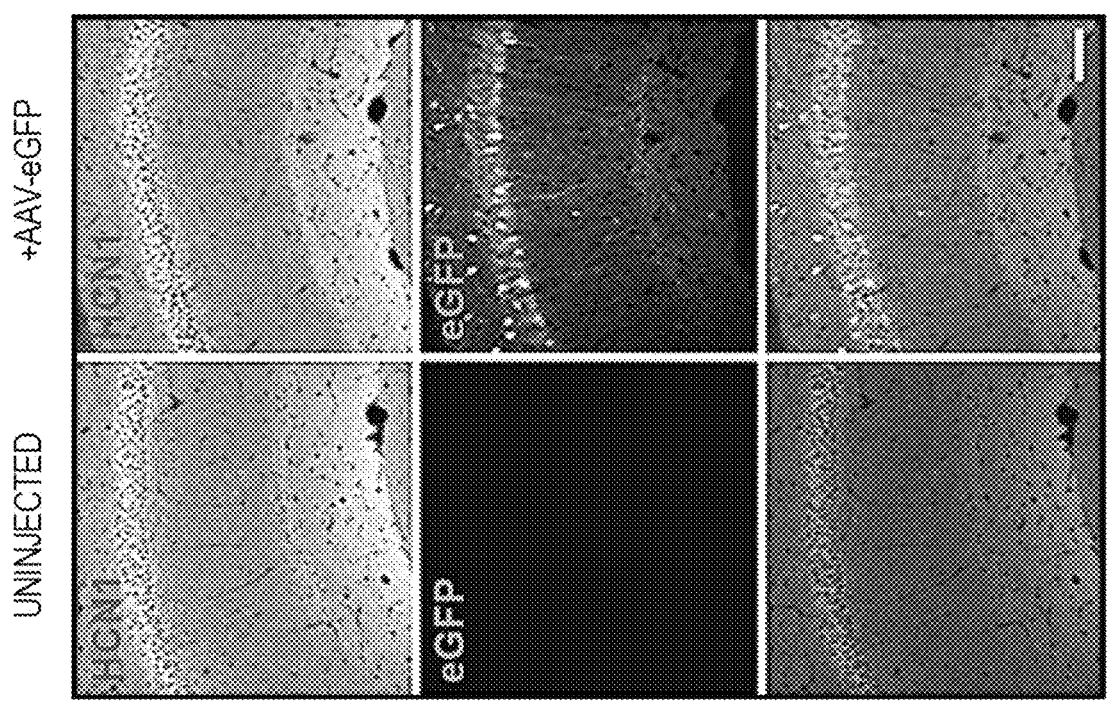
FIG. 6A and FIG. 6B together illustrate that AAV-eGFP fails to rescue distal dendritic targeting of either HCN1 or HCN2 in TRIP8b KO mice. The hippocampi of TRIP8b KO mice were unilaterally injected with AAV-eGFP to examine effects on dendritic targeting of HCN1 (FIG. 6A) and HCN2 (FIG. 6B). Left hand panels show uninjected (control) hemisphere and right hand panels show the injected hemisphere. Top panels are stained for HCN1 or HCN2 (red), middle panels for eGFP (green), and the lower panels are a composite image of the two. Note that the injected hemisphere shows no difference in HCN1 or HCN2 staining in the SLM relative to the uninjected hemisphere. Scale bar represents 100 μm.
Figure 6A:
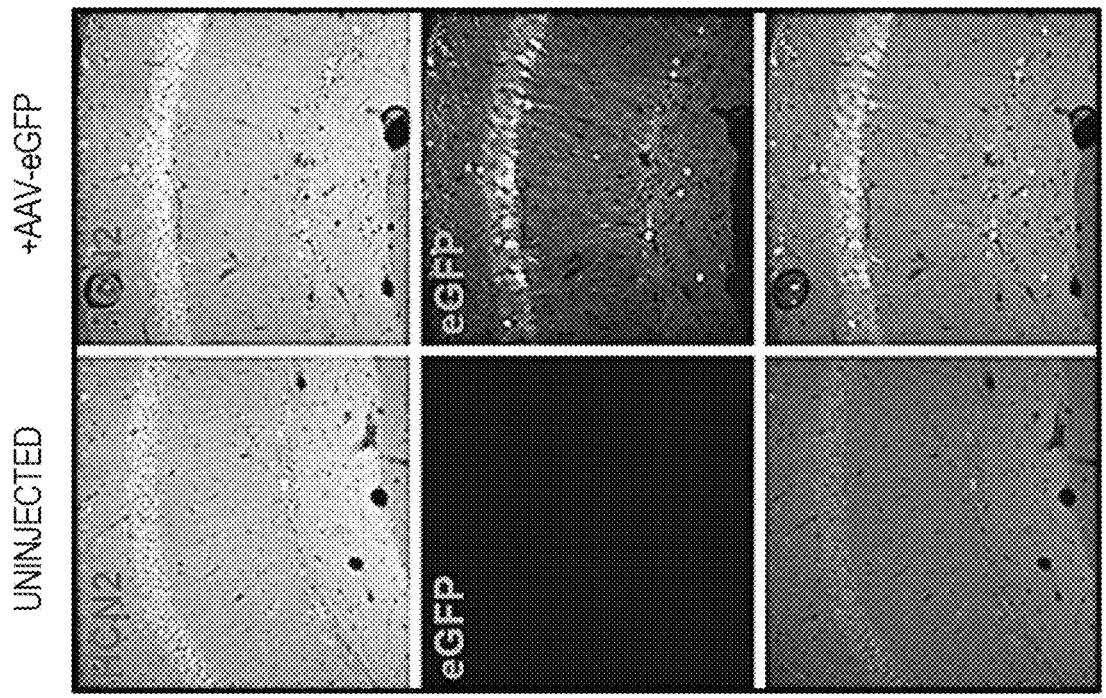
Figure 7C:
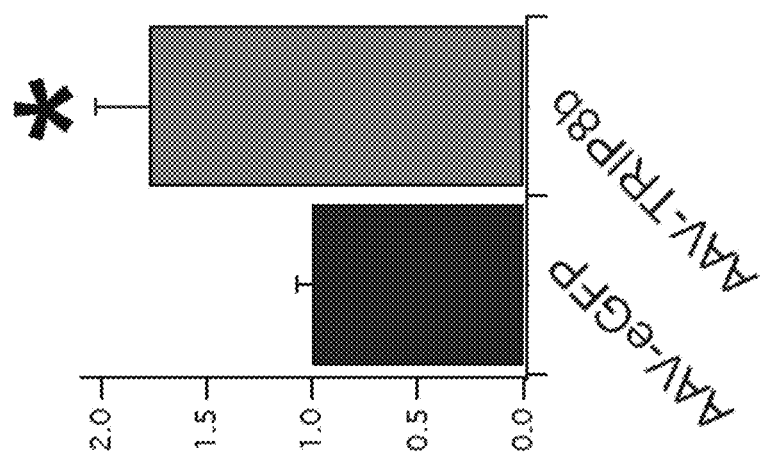
FIG. 7A, FIG. 7B, and FIG. 7C together illustrate that AAV-TRIP8b increases HCN1 and HCN2 total protein expression in the hippocampi of TRIP8b KO mice.
Figure 7B:
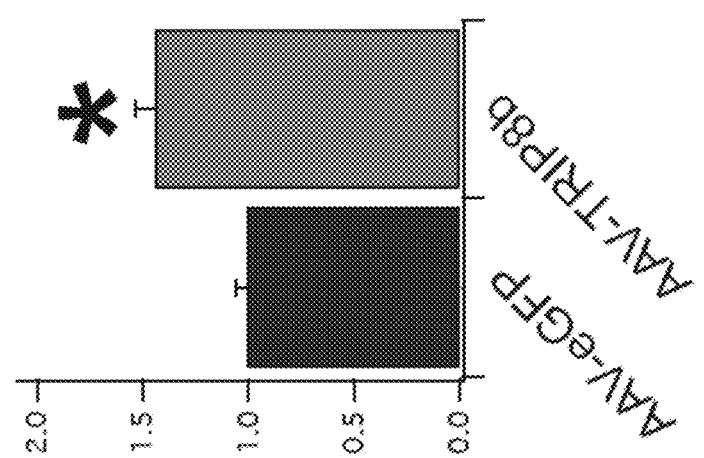
Figure 7A:
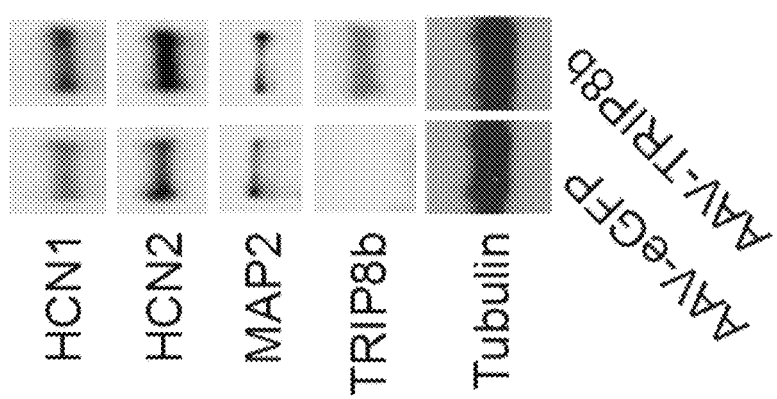

After determining that AAV-TRIP8b was sufficient to rescue somatic $I_h$, we next investigated its effect on distal dendritic enrichment by unilaterally injecting the viral constructs in TRIP8b KO mice and performing immunohistochemistry (IHC). In the uninjected hemisphere of all conditions, the distal dendritic enrichment of HCN1 and HCN2 was markedly reduced, similar to our previous findings[16]. In TRIP8b KO mice injected with AAV-eGFP, no distal dendritic enrichment of HCN1 or HCN2 was noted in the injected hemisphere. (See FIG. 6). In contrast, unilateral injection of AAV-TRIP8b led to successful rescue of the distal dendritic enrichment of HCN1 and HCN2 (FIG. 2A). To quantify this effect, we scaled the magnitude of HCN1 staining in the injected hemisphere by the staining in the uninjected hemisphere using regions of interest (ROI) drawn over each anatomic structure. (See FIG. 6B). As expected, AAV-TRIP8b produced an increase in HCN1 staining in the distal dendrites of the SLM (see FIG. 6B) and in HCN protein on western blot. (See FIG. 7). These experiments demonstrate that viral rescue of TRIP8b in the hippocampus is sufficient to rescue HCN channel trafficking.

Figure 8:
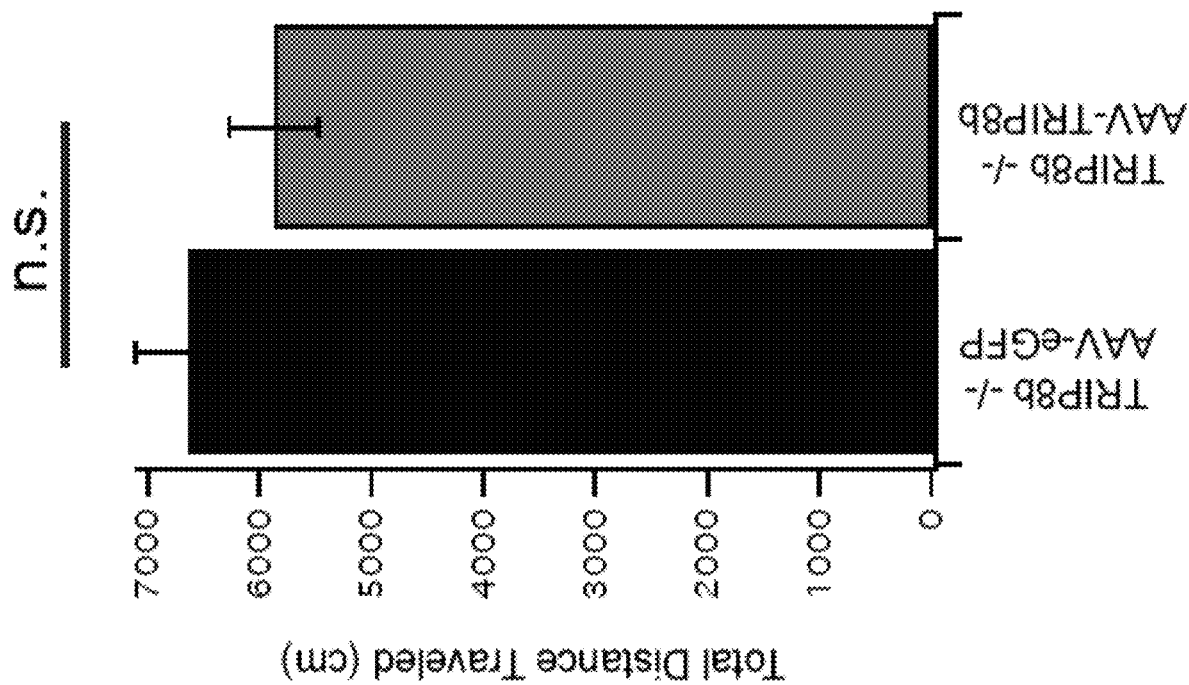
FIG. 8 illustrates that open field test reveals no difference between bilateral injection of AAV-TRIP8b and AAV-eGFP. TRIP8b KO mice were bilaterally injected with either AAV-TRIP8b or AAV-eGFP. After 4 weeks, an open field test was performed to determine if there were any differences in locomotor activity. Mice injected with AAV-eGFP (6632±473 cm, n=6) showed no difference in total distance traveled relative to mice injected with AAV-TRIP8b (5864±399 cm, n=6) by two tailed T test ($p>0.05$). Data reported and displayed as mean±s.e.m.
Figure 9A:
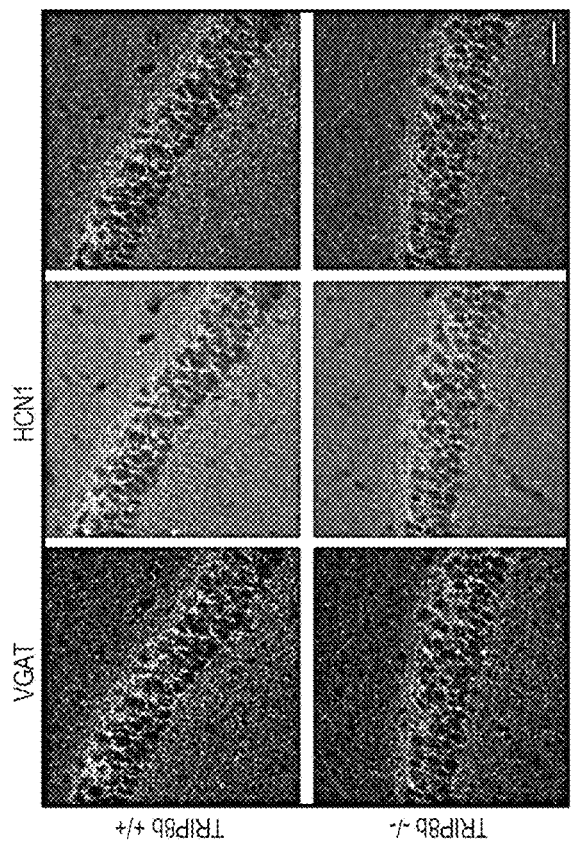
FIG. 9A and FIG. 9B together illustrate that presynaptic inhibitory terminals in CA1 express HCN1 in a TRIP8b independent manner.
Figure 9B:
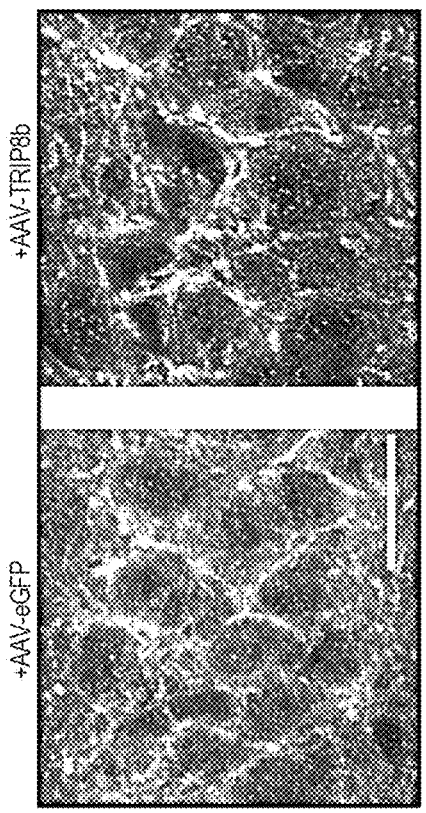

CA1 presynaptic inhibitory terminals express HCN1 in a TRIP8b independent manner. Incidentally, we noted that HCN1 expression in the cell body layer of CA1 appeared punctate, suggesting that it was expressed by terminals synapsing onto the cell bodies of CA1 pyramidal neurons. We next performed immunohistochemistry to confirm that indeed, the majority of HCN1 in the cell body layer is co-localized with vesicular GABA transporter (vGAT) positive inhibitory terminals. (See FIG. 8). Similar experiments using a presynaptic excitatory marker (vGlut) and postsynaptic markers (PSD95, Gephrin) did not show colocalization (data not shown). As has been seen at other presynaptic terminals expressing HCN1 {Huang:2012gp}, this pattern of expression was not changed in TRIP8b KO mice, suggesting that TRIP8b is not responsible for trafficking HCN1 in these interneurons. Given that we used a synapsin promoter in our AAV constructs, it remained possible that exogenous expression of TRIP8b in the interneurons may affect HCN1 trafficking. However, we did not observe any change in the presynaptic localization of HCN1 after treatment with either AAV-eGFP or AAV-TRIP8b. (See FIG. 7). Given that HCN1 expression in CA1 interneurons did not change with genetic knockout of TRIP8b or viral expression of TRIP8b, we did not pursue these findings further.

Figure 2C:
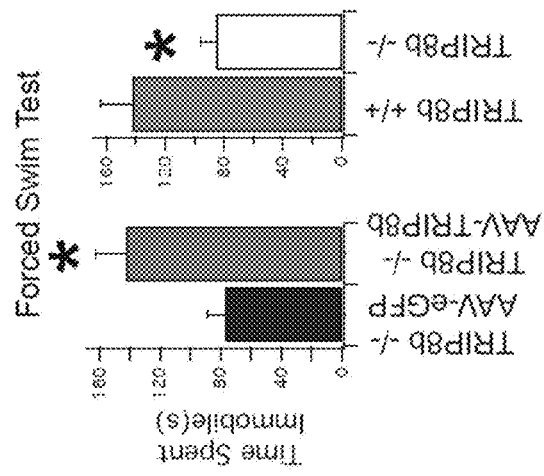
Figure 2D:
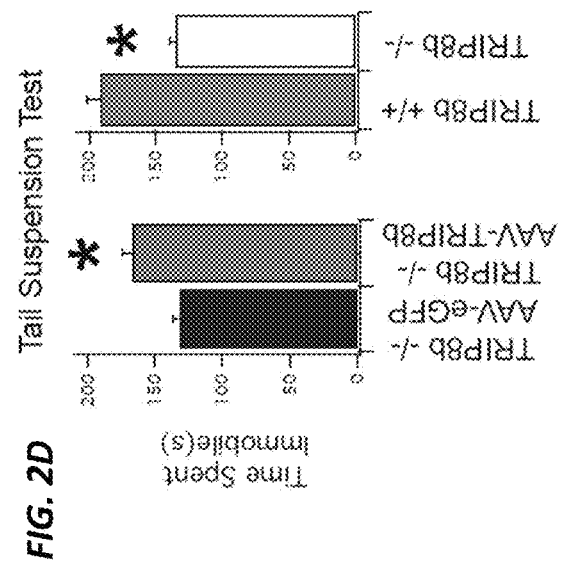

Loss of the distal dendritic enrichment of HCN channels in CA1 is responsible for the increase in antidepressant-like behavior of TRIP8b KO mice. Previous reports have found that reduction of HCN channel expression by HCN1 or HCN2 knockout[16] leads to antidepressant-like effects on behavior in two common antidepressant screening tests: the Forced Swim Test (FST) and Tail Suspension Test (TST). Because genetic ablation of TRIP8b[16] and siRNA knockdown of HCN1 in CA1 pyramidal neurons[17] also lead to antidepressant-like effects on behavior, we reasoned there could be a specific link between antidepressant-like behavioral effects and the distal dendritic enrichment of HCN channels in CA1 dendrites. We next examined if rescuing the distal dendritic enrichment of HCN channels influenced performance on TST and FST. We injected the CA1 of TRIP8b KO mice bilaterally with either an AAV-eGFP control or AAV-TRIP8b, which restored HCN channel distal dendritic enrichment in CA1 pyramidal neurons. We then performed FST and TST (FIG. 2C and FIG. 2D). As demonstrated previously, TRIP8b KO mice have reduced immobility time on both FST and TST compared to WT littermates. TRIP8b KO mice injected with AAV-TRIP8b showed increased immobility time on TST and FST compared to AAV-eGFP injected controls, indicating a reversal of the antidepressant-like behavior normally observed in TRIP8b KO mice. As a control for locomotor function, we also performed an open field test. (See FIG. 8). Consistent with a specific effect on TST and FST, no differences were observed between AAV-eGFP and AAV-TRIP8b treated mice. Our results indicate that rescuing the distal dendritic enrichment of HCN channels with bilateral AAV-TRIP8b injection is sufficient to reverse the behavioral phenotype of TRIP8b KO mice specifically via effects on the distal dendrites.

Both TRIP8b binding sites are required for distal dendritic enrichment of HCN channels. We next set out to identify the TRIP8b domains that are necessary for HCN channel trafficking. All TRIP8b isoforms bind to HCN subunits at two distinct locations. First, there is an interaction between the cyclic nucleotide binding domain (CNBD) of HCN channels and an acidic stretch of amino acids N-terminal to the tetratricopeptide repeat (TPR) domains of TRIP8b15, 23. Second, the TPR domains of TRIP8b bind to the C-terminal tail of HCN. To examine the role of each interaction site in vivo we generated AAVs to express TRIP8b mutants designed to selectively eliminate each binding site. We previously demonstrated that deletion of 58 amino acids in the N-terminal portion of TRIP8b common to all isoforms (TRIP8b(Δ58)) disrupts interaction with the CNBD of HCN subunits without blocking the interaction between TRIP8b and the HCN subunit C-terminal tail[19]. Conversely, mutation of a key asparagine residue in the C-terminal portion of TRIP8b—the 13th residue of the third TPR domain (N13A)—disrupts binding to HCN subunit C-terminal tails while leaving the CNBD interaction intact[19]. To determine the importance of each TRIP8b-HCN interaction site for HCN channel surface trafficking in vivo, we performed whole cell recordings from TRIP8b KO mice bilaterally injected with AAV-eGFP, AAV-TRIP8b(N13A) (FIG. 3A, hereafter referred to be as AAV-N13A), or AAV-TRIP8b (Δ58) (FIG. 3A, hereafter referred to be as AAV-Δ58). Interestingly, mutation of either binding site prevented the TRIP8b constructs from successfully rescuing the sag ratio (FIG. 3B and FIG. 3D) or $I_h$ amplitude (FIG. 3C and FIG. 3E), indicating that both sites are necessary for TRIP8b-mediated upregulation of $I_h$ in vivo.

Although $I_h$ was not affected in our whole cell recordings, it remained possible that dendritic targeting of the channels the CNBD and C-terminal tail binding sites is required to maintain proper distal dendritic enrichment of HCN channels in vivo. In addition, both interaction sites are also necessary for reversing the antidepressant-like behavior of TRIP8b KO mice. Finally, the surprising finding that the N13A mutation, which prohibits TRIP8b interaction with the HCN subunit C-terminal tail, actively inhibits the distal dendritic enrichment of HCN channels hints at a novel regulatory mechanism of HCN channel trafficking. These results show that manipulations of TRIP8b-HCN coupling lead to changes in the distal dendritic enrichment of the channels and that this distal dendritic trafficking is inversely correlated with antidepressant-like behavior.

TABLE 2

| Genotype | Virus | Membrane Resistance, MΩ | Resting Membrane Potential, mV | Half Activation Potential, mV | Time Constant, ms |
|---|---|---|---|---|---|
| TRIP8b KO | AAV-eGFP | 376.8 (87.3, 9) | −67.4 (2.9, 9) | −99.55 (4.3, 7) | 250 (28, 7) |
| TRIP8b KO | AAV-N13A | 313.7 (61.2, 7) | −68.3 (3.4,7) | −101.4 (2.0, 7) | 269 (55, 7) |
| TRIP8b KO | AAV-Δ58 | 254.9 (29.9, 6) | −73.4 (1.3, 6) | −94.62 (4.1, 4) | 301 7, 5) | was restored. This can occur because somatic recordings of CA1 pyramidal neurons are unlikely to detect changes in ion channel function in the distal dendrites {Piskorowski: 2011jm}. We next unilaterally injected TRIP8b KO mice with one of the viral constructs mentioned above (AAV-eGFP, AAV-N13A, AAV-Δ58), or AAV-TRIP8b(Δ58/N13A), a double mutant lacking the ability to bind HCN subunits at either binding site (FIG. 3A, hereafter referred to be as an AAV-Δ58/N13A). We then performed IHC and quantified our images as above. We found that none of the mutants could restore HCN subunit distal dendritic enrichment (FIG. 4 for HCN1, see FIG. 10 for HCN2). These results indicate that both TRIP8b-HCN interaction sites are necessary for HCN channel distal dendritic enrichment.

Surprisingly, AAV-N13A decreased dendritic HCN1 signal intensity relative to AAV-eGFP injected TRIP8b KO mice, suggesting that the isolated loss of the interaction between TRIP8b and the HCN C-terminal tail may actively restrict dendritic targeting of HCN channels. We subsequently performed western blots from hippocampi of TRIP8b KO mice bilaterally injected with each TRIP8b mutant and noted a reduction in HCN1 and HCN2 total protein after injection with AAV-N13A relative to other conditions. (See FIG. 11), confirming a 'gain-of-function' effect of the AAV-N13A mutant to actively reduce total HCN protein levels.

Figure 12:
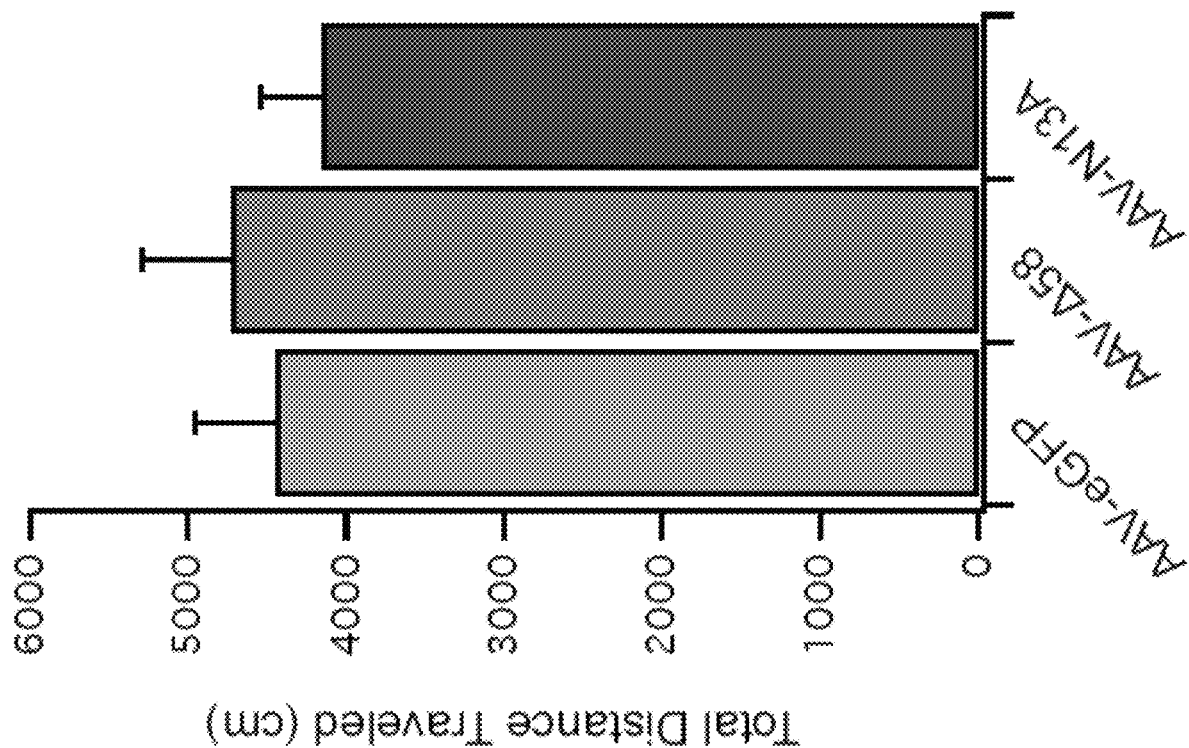
FIG. 12 illustrates that bilateral injection of AAV-eGFP, AAV-N13A, or AAV-Δ58 does not increase locomotor activity on open field test. TRIP8b KO animals were bilaterally injected with AAV-eGFP, AAV-N13A, or AAV-Δ58 (n=5,5,5). One month later the locomotor activity of the mice was assayed by open field testing. Total distance traveled in centimeters was recorded, although no difference between the three conditions was observed by one way ANOVA ($F(2,12)=0.32$, $p>0.5$). Data shown as mean±s.e.m.

Since the mutant TRIP8b constructs failed to rescue distal dendritic enrichment, we reasoned they should not reverse the antidepressant-like behavior of TRIP8b KO mice. We bilaterally injected TRIP8b KO mice with AAV-N13A, AAV-Δ58, or AAV-eGFP as a control. Consistent with our electrophysiological and IHC results, bilateral injection of AAV-Δ58 did not produce a change in either TST or FST (FIG. 4). Remarkably, expression of AAV-N13A, which diminished dendritic HCN channel expression without affecting somatic $I_h$, reduced the immobility time during FST and TST even more than in KO animals injected with AAV-eGFP. To ensure that these differences in FST and TST were not the result of increased locomotor activity, we performed an open field test. (See FIG. 12) and detected no differences in locomotion between groups. These results demonstrate that the interaction between TRIP8b and both Table 2 provides a summary of membrane properties from CA1 pyramidal neurons infected with AAV-N13A or AAV-Δ58. Table 2 displays the membrane properties of CA1 pyramidal neurons from TRIP8b KO mice infected with AAV-eGFP, AAV-N13A, or AAV-Δ58. Note that the information for the AAV-eGFP condition is identical to that presented in Table S1 but is reproduced here for comparison. A one way ANOVA comparing the three conditions for each parameter was not significant (p>0.05 in all cases). Data presented as Mean (s.e.m., n).

Discussion

Genetic knockout of HCN1 or HCN2[16], as well as siRNA knockdown of HCN1 in the CA1[17], leads to antidepressant-like effects on behavior in the TST and FST. Importantly, the antidepressant-like behavior of the HCN1 and HCN2 KO mice is also observed in TRIP8b KO mice[16]. Because a critical role for TRIP8b in the CA1 is to facilitate the proper subcellular trafficking of HCN channels, these results suggest that the distal dendritic enrichment of HCN channels produced by TRIP8b is particularly relevant for influencing antidepressant-like behaviors. In this paper, we demonstrate that manipulating the distal dendritic enrichment of HCN channels in CA1 is sufficient to influence antidepressant-like behaviors. Bilateral injection of AAV-TRIP8b restored the distal dendritic enrichment of HCN channels and reversed the antidepressant-like behaviors of TRIP8b knockout while bilateral injection of AAV-N13A reduced the distal dendritic enrichment of HCN channels and promoted antidepressant-like behaviors. These results establish that bidirectionally manipulating the subcellular distribution of HCN channels in the CA1 is sufficient to affect antidepressant-like behaviors.

Other studies have also pointed to a role for HCN channels in depression. Mice subjected to Chronic Social Defeat (CSD) stress develop depression-like behaviors, and a recent report demonstrated that $I_h$ is significantly upregulated in NAc-projecting, VTA dopaminergic neurons[24]. Interestingly, chronic SSRI administration reduced the increase in $I_h$ caused by CSD stress[25]. Corticotropin releasing factor, which has been implicated in depression pathogenesis through HPA axis dysfunction[26], increases $I_h$ in both the basolateral amygdala and paraventricular nucleus of the hypothalamus[27, 28]. While evidence is accumulating for involvement of HCN channels in depression models, it remains to be determined if upregulation of HCN channels in distinct brain regions underlies depression. Future studies should also indicate whether upregulation of HCN or TRIP8b in hippocampal area CA1 occurs in MDD patients or rodent models and whether reducing HCN channel function in the hippocampus underlies any of the clinical effects of monoamine reuptake inhibitors.

The precise mechanism for how removal of dendritic HCN channels produces antidepressant-like behavior remains unclear. An accumulating body of evidence suggests that MDD is caused by dysfunction in many identifiable neuronal circuits. One recent report showed that chronic stress decreased both CA1 and hippocampal network excitability and that this decrease was reversible with antidepressants[29]. Loss of HCN channels from hippocampal distal dendrites increases temporal summation and cellular excitability, and in the context of the neuronal circuit hypothesis, increasing hippocampal network excitability is a plausible mechanism by which loss of HCN channels could influence antidepressant-like behavior. In addition, the specific localization of HCN channels to the SLM portion of the apical dendrites may confer a pathway specific regulation of excitability. Chronic stress in mice decreases EPSPs in the SLM of CA1 pyramidal cells through AMPA-R downregulation[30]. In addition, chronic SSRI treatment specifically reverses these AMPA-R mediated decreases in excitability of SLM synapses without changing the excitability of synapses in the SR[31]. Because HCN channels are enriched in the SLM where they constrain excitability of temporoammonic inputs, loss of HCN channels in these distal dendrites could reverse or mitigate pathway specific synaptic weakening that may play a role in depression-like behaviors.

In this paper, we establish the distal dendritic enrichment of HCN channels in CA1 pyramidal neurons as a key determinant of performance in the tail suspension test and forced swim test. For therapeutic purposes, it is significant to note that therapies aimed at disrupting either TRIP8b-HCN interaction site are predicted to limit trafficking of HCN channels and produce an increase in antidepressant-like behavior. Recent efforts have been directed at finding small molecule inhibitors of the interaction between the TPR domains of TRIP8b and the C terminal tripeptide of HCN channel pore forming subunits{Han:2015fw}. Given the brain specific expression pattern of TRIP8b, this strategy should limit cardiac effects seen with systemic HCN channel inhibitors. Overall, our results indicate that disrupting the distal dendritic enrichment of HCN channels through manipulations that impair TRIP8b-HCN interactions represents a promising target for future antidepressant therapies {Han:2015fw}.

REFERENCES

1. Kessler R C, Berglund P, Demler O, Jin R, Merikangas K R, Walters E E. Lifetime prevalence and age-of-onset distributions of DSM-IV disorders in the National Comorbidity Survey Replication. Arch Gen Psychiatry 2005; 62: 593-602.
2. Lépine J-P, Briley M. The increasing burden of depression. Neuropsychiatr Dis Treat 2011; 7: 3-7.
3. Krishnan V, Nestler E J. The molecular neurobiology of depression. Nature 2008; 455: 894-902.
4. Duman R S, Aghajanian G K. Synaptic Dysfunction in Depression: Potential Therapeutic Targets. Science 2012; 338: 68-72.
5. Russo S J, Nestler E J. The brain reward circuitry in mood disorders. Nat Rev Neurosci 2013; 14: 609-625.
6. Newport D J, Carpenter L L, McDonald W M, Potash J B, Tohen M, Nemeroff C B et al. Ketamine and other NMDA antagonists: early clinical trials and possible mechanisms in depression. Am J Psychiatry 2015; 172: 950-966.
7. Papakostas G I, Ionescu D F. Towards new mechanisms: an update on therapeutics for treatment-resistant major depressive disorder. Mol Psychiatry 2015; 20: 1142-1150.
8. Biel M, Wahl-Schott C, Michalakis S, Zong X. Hyperpolarization-activated cation channels: from genes to function. Physiol Rev 2009; 89: 847-885.
9. Wahl-Schott C, Biel M. HCN channels: structure, cellular regulation and physiological function. Cell Mol Life Sci 2009; 66: 470-494.
10. Magee J C. Dendritic hyperpolarization-activated currents modify the integrative properties of hippocampal CA1 pyramidal neurons. J Neurosci 1998; 18: 7613-7624.
11. Magee J. Dendritic Ih normalizes temporal summation in hippocampal CA1 neurons. Nat Neurosci 1999; 2: 848-848.
12. Tsay D, Dudman J T, Siegelbaum S A. HCN1 channels constrain synaptically evoked Ca2+ spikes in distal dendrites of CA1 pyramidal neurons. Neuron 2007; 56: 1076-1089.
13. Santoro B, Piskorowski R A, Pian P, Hu L, Liu H, Siegelbuam S A. TRIP8b splice variants form a family of auxiliary subunits that regulate gating and trafficking of HCN channels in the brain. Neuron 2009; 62: 802-813.
14. Zolles G, Wenzel D, Bildl W, Schulte U, Hofmann A, Muller C S et al. Association with the auxiliary subunit PEX5R/Trip8b controls responsiveness of HCN channels to cAMP and adrenergic stimulation. Neuron 2009; 62: 814-825.
15. Lewis A S, Schwartz E, Chan C S, Noam Y, Shin M, Wadman W J et al. Alternatively spliced isoforms of TRIP8b differentially control h channel trafficking and function. J Neurosci 2009; 29: 6250-6265.
16. Lewis A S, Vaidya S P, Blaiss C A, Liu Z, Stoub T R, Brager D H et al. Deletion of the hyperpolarization-activated cyclic nucleotide-gated channel auxiliary subunit TRIP8b impairs hippocampal Ih localization and function and promotes antidepressant behavior in mice. J Neurosci 2011; 31: 7424-7440.
17. Kim C S, Chang P Y, Johnston D. Enhancement of dorsal hippocampal activity by knockdown of HCN1 channels leads to anxiolytic- and antidepressant-like behaviors. Neuron 2012; 75: 503-516.
18. Santoro B, Hu L, Liu H, Saponaro A, Pian P, Piskorowski R A et al. TRIP8b regulates HCN1 channel trafficking and gating through two distinct C-terminal interaction sites. J Neurosci 2011; 31: 4074-4086.
19. Han Y, Noam Y, Lewis A S, Gallagher J J, Wadman W J, Baram T Z et al. Trafficking and gating of hyperpolarization-activated cyclic nucleotide-gated channels are regulated by interaction with tetratricopeptide repeat-containing Rab8b-interacting protein (TRIP8b) and cyclic AMP at distinct sites. J Biol Chem 2011; 286: 20823-20834.
20. Aschauer D F, Kreuz S, Rumpel S. Analysis of Transduction Efficiency, Tropism and Axonal Transport of AAV Serotypes 1, 2, 5, 6, 8 and 9 in the Mouse Brain. PLoS ONE 2013; 8: e76310.
21. Heuermann R J, Jaramillo T C, Ying S-W, Suter B A, Lyman K A, Han Y et al. Reduction of thalamic and cortical Ih by deletion of TRIP8b produces a mouse model of human absence epilepsy. Neurobiol Dis 2016; 85: 81-92.
22. Piskorowski R, Santoro B, Siegelbaum S A. TRIP8b splice forms act in concert to regulate the localization and expression of HCN1 channels in CA1 pyramidal neurons. Neuron 2011; 70: 495-509.
23. Saponaro A, Pauleta S R, Cantini F, Matzapetakis M, Hammann C, Donadoni C et al. Structural basis for the mutual antagonism of cAMP and TRIP8b in regulating HCN channel function. Proc Natl Acad Sci USA 2014; 111: 14577-14582.
24. Friedman A K, Walsh J J, Juarez B, Ku S M, Chaudhury D, Wang J et al. Enhancing depression mechanisms in midbrain dopamine neurons achieves homeostatic resilience. Science 2014; 344: 313-319
25. Cao J L, Covington H E, Friedman A K, Wilkinson M B, Walsh J J, Cooper D C et al. Mesolimbic Dopamine Neurons in the Brain Reward Circuit Mediate Susceptibility to Social Defeat and Antidepressant Action. J Neurosci 2010; 30: 16453-16458.
26. Joels M, Baram T Z. The neuro-symphony of stress. Nat Rev Neurosci 2009; 10: 459-466.
27. Qiu D L, Chu C P, Shirasaka T, Tsukino H, Nakao H, Kato K et al. Corticotrophin-releasing factor augments the IH in rat hypothalamic paraventricular nucleus parvocellular neurons in vitro. J Neurophysiol 2005; 94: 226-234
28. Giesbrecht C J, Mackay J P, Silveira H B, Urban J H, Colmers Countervailing Modulation of Ih by Neuropeptide Y and Corticotrophin-Releasing Factor in Basolateral Amygdala As a Possible Mechanism for Their Effects on Stress-Related Behaviors. J Neurosci 2010; 30: 16970-16982.
29. Stepan J, Hladky F, Uribe A, Holsboer F, Schmidt M V, Eder M. High-Speed imaging reveals opposing effects of chronic stress and antidepressants on neuronal activity propagation through the hippocampal trisynaptic circuit. Front Neural Circuits 2015; 9: 819.
30. Kallarackal A J, Kvarta M D, Cammarata E, Jaberi L, Cai X, Bailey A M et al. Chronic Stress Induces a Selective Decrease in AMPA Receptor-Mediated Synaptic Excitation at Hippocampal Temporoammonic-CA1 Synapses. J Neurosci 2013; 33: 15669-15674.
31. Cai X, Kallarackal A J, Kvarta M D, Goluskin S, Gaylor K, Bailey A M et al. Local potentiation of excitatory synapses by serotonin and its alteration in rodent models of depression. Nat Neurosci 2013; 16: 464-472.
32. Shin M, Simkin D, Suyeoka G M, Chetkovich D M. Evaluation of HCN2 abnormalities as a cause of juvenile audiogenic seizures in Black Swiss mice. Brain Res 2006; 1083: 14-20.
33. Shin M, Chetkovich D M. Activity-dependent regulation of h channel distribution in hippocampal CA1 pyramidal neurons. J Biol Chem 2007; 282: 33168-33180.
34. Chung W K, Shin M, Jaramillo T C, Leibel R L, LeDuc C A, Fischer S G et al. Absence epilepsy in apathetic, a spontaneous mutant mouse lacking the h channel subunit, HCN2. Neurobiol Dis 2009; 33: 499-508.

Example 2

Blocking cAMP Binding to Hyperpolarization Activated Cyclic Nucleotide Gated (HCN) Channels Increases Anti-Depressant-Like Behavior in Mice Introduction Hyperpolarization activated cyclic nucleotide gated (HCN) channels respond to changes in intracellular cyclic adenosine monophosphate levels (cAMP). In particular, increasing concentrations of cAMP lead to more channel opening. Based on our existing data showing that inhibiting the function of HCN channels in the brain leads to antidepressant-like behavior, we hypothesized that blocking cAMP binding to HCN would also increase antidepressant-like behavior.

In order to study cAMP binding to HCN channels, we generated a novel knock-in animal with a mutation in the HCN2 gene (Hcn2$^{+/+}$ animals) that prevents cAMP from binding the channel (HCN2(R591E)). To study the effect of mutating the channel, we next performed the tail suspension test (TST) and forced swim test (FST) on mature (2-6 month old) animals.

Experimental Results

Figure 13:
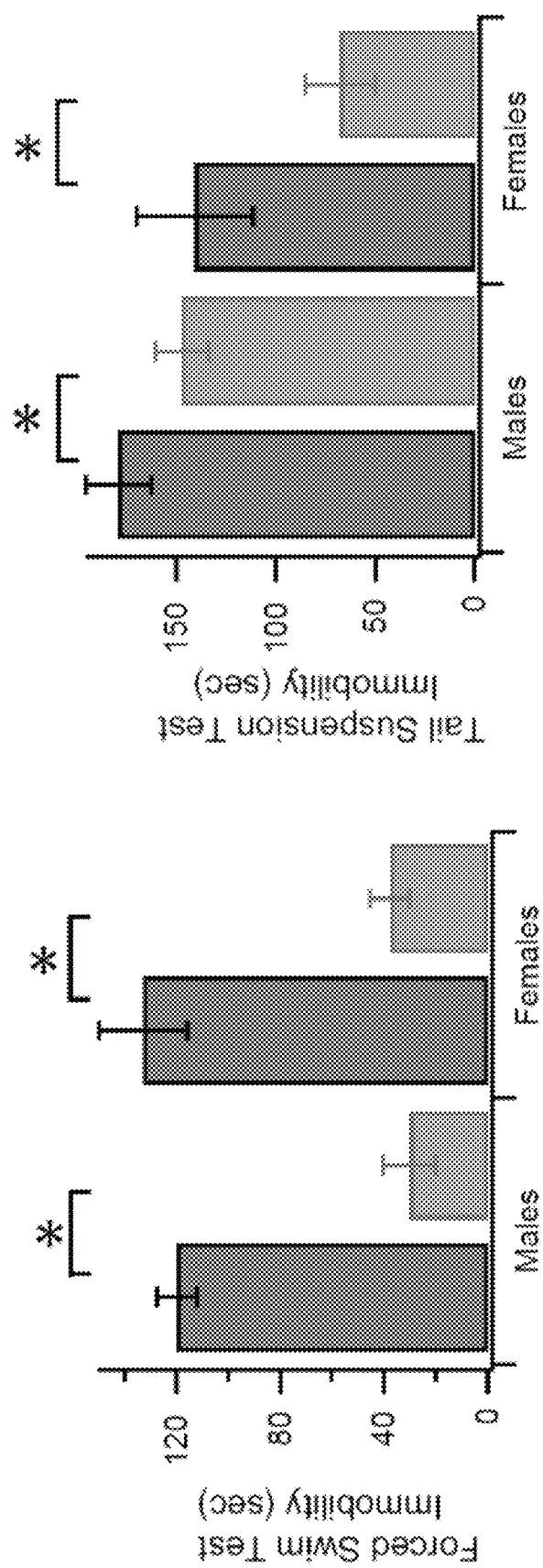
FIG. 13 illustrates that mice with a point mutation in HCN2 that limits channel function exhibit antidepressant-like changes in behavior.

Forced swim task. Hcn2$^{+/+}$ animals showed more time immobile (males: 120±7.63, females 132.8±16.99, n=5, 5) than Hcn2$^{R591E/R591E}$ animals (males: 30±10.27, females: 37.43±7.64, n=6, 20). (See FIG. 13). Because the HCN2 (R591E) mutation limits HCN channel function and reduces the number of active channels at the cell surface, this suggests that limiting HCN channels is likely to have an antidepressant-like effect on behavior, A two way ANOVA comparing gender and genotype showed an effect of genotype (F(1,28)=69.7, p<0.05) but did not show an effect of gender (F(1,28)=0.84, p=0.36) nor an interaction between the two (F(1,28)=0.06, p=0.80).

Tail suspension task. Hcn2$^{+/+}$ animals showed more time immobile (males: 170±16.32, females 140.66±29.23, n=5, 3) than Hcn2$^{R591E/R591E}$ animals (males: 147±13.44, females: 67.60±17.57, n=6,3). (See FIG. 13). A two way ANOVA comparing gender and genotype indicated a main effect of gender (F(1,20)=7.95, p<0.05) and genotype (F(1, 20)=6.32, p<0.05) but no interaction between the two (F(1, 20)=0.96, p=0.33). All data presented as mean±sem.

CONCLUSION

These results indicated that loss of cAMP modulation of HCN channels increases antidepressant-like behavior and further strengthen the case that HCN channels are a target for the treatment of depression.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations that is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

The invention claimed is:

1. An adeno-associated viral vector comprising a nucleic acid encoding a variant of tetratricopeptide repeat (TPR)-containing Rab8b interacting (TRIP8b) protein, wherein the variant of TRIP8b protein comprises an amino acid substitution mutation in the tetratricopeptide repeat (TPR) that disrupts binding of the TPR with the C-terminus of the hyperpolarization-activated cyclic nucleotide gated (HCN) channel or subunits thereof, wherein the variant of TRIP8b comprises the amino acid sequence selected from SEQ ID NO: 2, SEQ ID NO: 3, SEQ ID NO: 4, or SEQ ID NO: 5, and wherein the vector comprises a promoter for expressing the variant of TRIP8b protein in neurons.

2. A pharmaceutical composition comprising the vector of claim 1 together with a suitable pharmaceutical carrier.

3. The vector of claim 1, wherein the promoter restricts expression of the variant of TRIP8b protein to neurons.

* * * * *

```
                        SEQUENCE LISTING

<160> NUMBER OF SEQ ID NOS: 10

<210> SEQ ID NO 1
<211> LENGTH: 344
<212> TYPE: PRT
<213> ORGANISM: Homo sapiens

<400> SEQUENCE: 1

Met Gln Ala Glu Trp Glu Glu Met Ala Arg Arg Asn Trp Ile Ser Glu
1               5                   10                  15

Asn Gln Glu Ala Gln Asn Gln Val Thr Ile Ser Ala Ser Glu Lys Gly
            20                  25                  30

Tyr Tyr Phe His Thr Glu Asn Pro Phe Lys Asp Trp Pro Gly Ala Phe
        35                  40                  45

Glu Glu Gly Leu Lys Arg Leu Lys Glu Gly Asp Leu Pro Val Thr Ile
    50                  55                  60

Leu Phe Met Glu Ala Ala Ile Leu Gln Asp Pro Gly Asp Ala Glu Ala
65                  70                  75                  80

Trp Gln Phe Leu Gly Ile Thr Gln Ala Glu Asn Glu Asn Glu Gln Ala
                85                  90                  95

Ala Ile Val Ala Leu Gln Arg Cys Leu Glu Leu Gln Pro Asn Asn Leu
            100                 105                 110

Lys Ala Leu Met Ala Leu Ala Val Ser Tyr Thr Asn Thr Gly His Gln
        115                 120                 125

Gln Asp Ala Cys Asp Ala Leu Lys Asn Trp Ile Lys Gln Asn Pro Lys
    130                 135                 140

Tyr Lys Tyr Leu Val Lys Ser Lys Lys Gly Ser Pro Gly Leu Thr Arg
145                 150                 155                 160

Arg Met Ser Lys Ser Pro Val Asp Ser Ser Val Leu Glu Gly Val Lys
                165                 170                 175

Glu Leu Tyr Leu Glu Ala Ala His Gln Asn Gly Asp Met Ile Asp Pro
            180                 185                 190

Asp Leu Gln Thr Gly Leu Gly Val Leu Phe His Leu Ser Gly Glu Phe
        195                 200                 205

Asn Arg Ala Ile Asp Ala Phe Asn Ala Ala Leu Thr Val Arg Pro Glu
    210                 215                 220

Asp Tyr Ser Leu Trp Asn Arg Leu Gly Ala Thr Leu Ala Asn Gly Asp
225                 230                 235                 240

Arg Ser Glu Glu Ala Val Glu Ala Tyr Thr Arg Ala Leu Glu Ile Gln
                245                 250                 255

Pro Gly Phe Ile Arg Ser Arg Tyr Asn Leu Gly Ile Ser Cys Ile Asn
            260                 265                 270

Leu Gly Ala Tyr Arg Glu Ala Val Ser Asn Phe Leu Thr Ala Leu Ser
        275                 280                 285

Leu Gln Arg Lys Ser Arg Asn Gln Gln Val Pro His Pro Ala Ile
    290                 295                 300

Ser Gly Asn Ile Trp Ala Ala Leu Arg Ile Ala Leu Ser Leu Met Asp
305                 310                 315                 320

Gln Pro Glu Leu Phe Gln Ala Ala Asn Leu Gly Asp Leu Asp Val Leu
                325                 330                 335
```

Leu Arg Ala Phe Asn Leu Asp Pro
            340

<210> SEQ ID NO 2
<211> LENGTH: 344
<212> TYPE: PRT
<213> ORGANISM: Artificial
<220> FEATURE:
<223> OTHER INFORMATION: Homo sapiens TPR3-N13A TRIP8b Variant

<400> SEQUENCE: 2

Met Gln Ala Glu Trp Glu Glu Met Ala Arg Arg Asn Trp Ile Ser Glu
1               5                   10                  15

Asn Gln Glu Ala Gln Asn Gln Val Thr Ile Ser Ala Ser Glu Lys Gly
            20                  25                  30

Tyr Tyr Phe His Thr Glu Asn Pro Phe Lys Asp Trp Pro Gly Ala Phe
        35                  40                  45

Glu Glu Gly Leu Lys Arg Leu Lys Glu Gly Asp Leu Pro Val Thr Ile
    50                  55                  60

Leu Phe Met Glu Ala Ala Ile Leu Gln Asp Pro Gly Asp Ala Glu Ala
65                  70                  75                  80

Trp Gln Phe Leu Gly Ile Thr Gln Ala Glu Asn Glu Asn Glu Gln Ala
                85                  90                  95

Ala Ile Val Ala Leu Gln Arg Cys Leu Glu Leu Gln Pro Asn Asn Leu
            100                 105                 110

Lys Ala Leu Met Ala Leu Ala Val Ser Tyr Thr Ala Thr Gly His Gln
        115                 120                 125

Gln Asp Ala Cys Asp Ala Leu Lys Asn Trp Ile Lys Gln Asn Pro Lys
    130                 135                 140

Tyr Lys Tyr Leu Val Lys Ser Lys Lys Gly Ser Pro Gly Leu Thr Arg
145                 150                 155                 160

Arg Met Ser Lys Ser Pro Val Asp Ser Ser Val Leu Glu Gly Val Lys
                165                 170                 175

Glu Leu Tyr Leu Glu Ala Ala His Gln Asn Gly Asp Met Ile Asp Pro
            180                 185                 190

Asp Leu Gln Thr Gly Leu Gly Val Leu Phe His Leu Ser Gly Glu Phe
        195                 200                 205

Asn Arg Ala Ile Asp Ala Phe Asn Ala Ala Leu Thr Val Arg Pro Glu
    210                 215                 220

Asp Tyr Ser Leu Trp Asn Arg Leu Gly Ala Thr Leu Ala Asn Gly Asp
225                 230                 235                 240

Arg Ser Glu Glu Ala Val Glu Ala Tyr Thr Arg Ala Leu Glu Ile Gln
                245                 250                 255

Pro Gly Phe Ile Arg Ser Arg Tyr Asn Leu Gly Ile Ser Cys Ile Asn
            260                 265                 270

Leu Gly Ala Tyr Arg Glu Ala Val Ser Asn Phe Leu Thr Ala Leu Ser
        275                 280                 285

Leu Gln Arg Lys Ser Arg Asn Gln Gln Val Pro His Pro Ala Ile
    290                 295                 300

Ser Gly Asn Ile Trp Ala Ala Leu Arg Ile Ala Leu Ser Leu Met Asp
305                 310                 315                 320

Gln Pro Glu Leu Phe Gln Ala Ala Asn Leu Gly Asp Leu Asp Val Leu
                325                 330                 335

Leu Arg Ala Phe Asn Leu Asp Pro
            340

<210> SEQ ID NO 3
<211> LENGTH: 344
<212> TYPE: PRT
<213> ORGANISM: Artificial
<220> FEATURE:
<223> OTHER INFORMATION: Homo sapiens TPR2-E15K TRIP8b Variant

<400> SEQUENCE: 3

Met Gln Ala Glu Trp Glu Met Ala Arg Arg Asn Trp Ile Ser Glu
1               5                   10                  15

Asn Gln Glu Ala Gln Asn Gln Val Thr Ile Ser Ala Ser Glu Lys Gly
            20                  25                  30

Tyr Tyr Phe His Thr Glu Asn Pro Phe Lys Asp Trp Pro Gly Ala Phe
        35                  40                  45

Glu Glu Gly Leu Lys Arg Leu Lys Glu Gly Asp Leu Pro Val Thr Ile
    50                  55                  60

Leu Phe Met Glu Ala Ala Ile Leu Gln Asp Pro Gly Asp Ala Glu Ala
65                  70                  75                  80

Trp Gln Phe Leu Gly Ile Thr Gln Ala Glu Asn Lys Asn Glu Gln Ala
                85                  90                  95

Ala Ile Val Ala Leu Gln Arg Cys Leu Glu Leu Gln Pro Asn Asn Leu
            100                 105                 110

Lys Ala Leu Met Ala Leu Ala Val Ser Tyr Thr Asn Thr Gly His Gln
        115                 120                 125

Gln Asp Ala Cys Asp Ala Leu Lys Asn Trp Ile Lys Gln Asn Pro Lys
    130                 135                 140

Tyr Lys Tyr Leu Val Lys Ser Lys Lys Gly Ser Pro Gly Leu Thr Arg
145                 150                 155                 160

Arg Met Ser Lys Ser Pro Val Asp Ser Ser Val Leu Glu Gly Val Lys
                165                 170                 175

Glu Leu Tyr Leu Glu Ala Ala His Gln Asn Gly Asp Met Ile Asp Pro
            180                 185                 190

Asp Leu Gln Thr Gly Leu Gly Val Leu Phe His Leu Ser Gly Glu Phe
        195                 200                 205

Asn Arg Ala Ile Asp Ala Phe Asn Ala Ala Leu Thr Val Arg Pro Glu
    210                 215                 220

Asp Tyr Ser Leu Trp Asn Arg Leu Gly Ala Thr Leu Ala Asn Gly Asp
225                 230                 235                 240

Arg Ser Glu Glu Ala Val Glu Ala Tyr Thr Arg Ala Leu Glu Ile Gln
                245                 250                 255

Pro Gly Phe Ile Arg Ser Arg Tyr Asn Leu Gly Ile Ser Cys Ile Asn
            260                 265                 270

Leu Gly Ala Tyr Arg Glu Ala Val Ser Asn Phe Leu Thr Ala Leu Ser
        275                 280                 285

Leu Gln Arg Lys Ser Arg Asn Gln Gln Gln Val Pro His Pro Ala Ile
    290                 295                 300

Ser Gly Asn Ile Trp Ala Ala Leu Arg Ile Ala Leu Ser Leu Met Asp
305                 310                 315                 320

Gln Pro Glu Leu Phe Gln Ala Ala Asn Leu Gly Asp Leu Asp Val Leu
                325                 330                 335

Leu Arg Ala Phe Asn Leu Asp Pro
            340

<210> SEQ ID NO 4

<211> LENGTH: 344
<212> TYPE: PRT
<213> ORGANISM: Artificial
<220> FEATURE:
<223> OTHER INFORMATION: Homo sapiens TPR5-N5A TRIP8b Variant

<400> SEQUENCE: 4

```
Met Gln Ala Glu Trp Glu Met Ala Arg Arg Asn Trp Ile Ser Glu
1               5                   10                  15

Asn Gln Glu Ala Gln Asn Gln Val Thr Ile Ser Ala Ser Glu Lys Gly
            20                  25                  30

Tyr Tyr Phe His Thr Glu Asn Pro Phe Lys Asp Trp Pro Gly Ala Phe
            35                  40                  45

Glu Glu Gly Leu Lys Arg Leu Lys Glu Gly Asp Leu Pro Val Thr Ile
        50                  55                  60

Leu Phe Met Glu Ala Ala Ile Leu Gln Asp Pro Gly Asp Ala Glu Ala
65              70                  75                  80

Trp Gln Phe Leu Gly Ile Thr Gln Ala Glu Asn Glu Asn Glu Gln Ala
                85                  90                  95

Ala Ile Val Ala Leu Gln Arg Cys Leu Glu Leu Gln Pro Asn Asn Leu
            100                 105                 110

Lys Ala Leu Met Ala Leu Ala Val Ser Tyr Thr Asn Thr Gly His Gln
            115                 120                 125

Gln Asp Ala Cys Asp Ala Leu Lys Asn Trp Ile Lys Gln Asn Pro Lys
        130                 135                 140

Tyr Lys Tyr Leu Val Lys Ser Lys Lys Gly Ser Pro Gly Leu Thr Arg
145             150                 155                 160

Arg Met Ser Lys Ser Pro Val Asp Ser Ser Val Leu Glu Gly Val Lys
                165                 170                 175

Glu Leu Tyr Leu Glu Ala Ala His Gln Asn Gly Asp Met Ile Asp Pro
            180                 185                 190

Asp Leu Gln Thr Gly Leu Gly Val Leu Phe His Leu Ser Gly Glu Phe
        195                 200                 205

Asn Arg Ala Ile Asp Ala Phe Asn Ala Ala Leu Thr Val Arg Pro Glu
    210                 215                 220

Asp Tyr Ser Leu Trp Ala Arg Leu Gly Ala Thr Leu Ala Asn Gly Asp
225             230                 235                 240

Arg Ser Glu Glu Ala Val Glu Ala Tyr Thr Arg Ala Leu Glu Ile Gln
                245                 250                 255

Pro Gly Phe Ile Arg Ser Arg Tyr Asn Leu Gly Ile Ser Cys Ile Asn
            260                 265                 270

Leu Gly Ala Tyr Arg Glu Ala Val Ser Asn Phe Leu Thr Ala Leu Ser
        275                 280                 285

Leu Gln Arg Lys Ser Arg Asn Gln Gln Val Pro His Pro Ala Ile
    290                 295                 300

Ser Gly Asn Ile Trp Ala Ala Leu Arg Ile Ala Leu Ser Leu Met Asp
305             310                 315                 320

Gln Pro Glu Leu Phe Gln Ala Ala Asn Leu Gly Asp Leu Asp Val Leu
                325                 330                 335

Leu Arg Ala Phe Asn Leu Asp Pro
            340
```

<210> SEQ ID NO 5
<211> LENGTH: 344
<212> TYPE: PRT
<213> ORGANISM: Artificial

<220> FEATURE:
<223> OTHER INFORMATION: Homo sapiens TPR6-R2A TRIP8b Variant

<400> SEQUENCE: 5

```
Met Gln Ala Glu Trp Glu Met Ala Arg Arg Asn Trp Ile Ser Glu
1               5                   10                  15

Asn Gln Glu Ala Gln Asn Gln Val Thr Ile Ser Ala Ser Glu Lys Gly
            20                  25                  30

Tyr Tyr Phe His Thr Glu Asn Pro Phe Lys Asp Trp Pro Gly Ala Phe
            35                  40                  45

Glu Glu Gly Leu Lys Arg Leu Lys Glu Gly Asp Leu Pro Val Thr Ile
        50                  55                  60

Leu Phe Met Glu Ala Ala Ile Leu Gln Asp Pro Gly Asp Ala Glu Ala
65              70                  75                  80

Trp Gln Phe Leu Gly Ile Thr Gln Ala Glu Asn Glu Asn Glu Gln Ala
            85                  90                  95

Ala Ile Val Ala Leu Gln Arg Cys Leu Glu Leu Gln Pro Asn Asn Leu
        100                 105                 110

Lys Ala Leu Met Ala Leu Ala Val Ser Tyr Thr Asn Thr Gly His Gln
            115                 120                 125

Gln Asp Ala Cys Asp Ala Leu Lys Asn Trp Ile Lys Gln Asn Pro Lys
        130                 135                 140

Tyr Lys Tyr Leu Val Lys Ser Lys Lys Gly Ser Pro Gly Leu Thr Arg
145                 150                 155                 160

Arg Met Ser Lys Ser Pro Val Asp Ser Ser Val Leu Glu Gly Val Lys
            165                 170                 175

Glu Leu Tyr Leu Glu Ala Ala His Gln Asn Gly Asp Met Ile Asp Pro
        180                 185                 190

Asp Leu Gln Thr Gly Leu Gly Val Leu Phe His Leu Ser Gly Glu Phe
            195                 200                 205

Asn Arg Ala Ile Asp Ala Phe Asn Ala Ala Leu Thr Val Arg Pro Glu
    210                 215                 220

Asp Tyr Ser Leu Trp Asn Arg Leu Gly Ala Thr Leu Ala Asn Gly Asp
225                 230                 235                 240

Arg Ser Glu Glu Ala Val Glu Ala Tyr Thr Arg Ala Leu Glu Ile Gln
            245                 250                 255

Pro Gly Phe Ile Ala Ser Arg Tyr Asn Leu Gly Ile Ser Cys Ile Asn
            260                 265                 270

Leu Gly Ala Tyr Arg Glu Ala Val Ser Asn Phe Leu Thr Ala Leu Ser
        275                 280                 285

Leu Gln Arg Lys Ser Arg Asn Gln Gln Val Pro His Pro Ala Ile
        290                 295                 300

Ser Gly Asn Ile Trp Ala Ala Leu Arg Ile Ala Leu Ser Leu Met Asp
305                 310                 315                 320

Gln Pro Glu Leu Phe Gln Ala Ala Asn Leu Gly Asp Leu Asp Val Leu
            325                 330                 335

Leu Arg Ala Phe Asn Leu Asp Pro
            340
```

<210> SEQ ID NO 6
<211> LENGTH: 344
<212> TYPE: PRT
<213> ORGANISM: Mus musculus

<400> SEQUENCE: 6

```
Met Gln Ala Glu Trp Glu Glu Met Ala Arg Arg Asn Trp Ile Ser Glu
1               5                  10                  15

Asn Gln Glu Ala Gln Asn Val Thr Val Ser Ala Ser Glu Lys Gly
            20                  25                  30

Tyr Tyr Phe His Thr Glu Asn Pro Phe Lys Asp Trp Pro Gly Ala Phe
            35                  40                  45

Glu Glu Gly Leu Lys Arg Leu Lys Glu Gly Asp Leu Pro Val Thr Ile
            50                  55                  60

Leu Phe Met Glu Ala Ala Ile Leu Gln Asp Pro Gly Asp Ala Glu Ala
65                  70                  75                  80

Trp Gln Phe Leu Gly Ile Thr Gln Ala Glu Asn Glu Asn Glu Gln Ala
                85                  90                  95

Ala Ile Val Ala Leu Gln Arg Cys Leu Glu Leu Gln Pro Asn Asn Leu
            100                 105                 110

Lys Ala Leu Met Ala Leu Ala Val Ser Tyr Thr Asn Thr Ser His Gln
            115                 120                 125

Gln Asp Ala Cys Glu Ala Leu Lys Asn Trp Ile Lys Gln Asn Pro Lys
            130                 135                 140

Tyr Lys Tyr Leu Val Lys Asn Lys Lys Gly Ser Pro Gly Leu Thr Arg
145                 150                 155                 160

Arg Met Ser Lys Ser Pro Val Asp Ser Ser Val Leu Glu Gly Val Lys
                165                 170                 175

Glu Leu Tyr Leu Glu Ala Ala His Gln Asn Gly Asp Met Ile Asp Pro
            180                 185                 190

Asp Leu Gln Thr Gly Leu Gly Val Leu Phe His Leu Ser Gly Glu Phe
            195                 200                 205

Asn Arg Ala Ile Asp Ala Phe Asn Ala Ala Leu Thr Val Arg Pro Glu
            210                 215                 220

Asp Tyr Ser Leu Trp Asn Arg Leu Gly Ala Thr Leu Ala Asn Gly Asp
225                 230                 235                 240

Arg Ser Glu Glu Ala Val Glu Ala Tyr Thr Arg Ala Leu Glu Ile Gln
                245                 250                 255

Pro Gly Phe Ile Arg Ser Arg Tyr Asn Leu Gly Ile Ser Cys Ile Asn
            260                 265                 270

Leu Gly Ala Tyr Arg Glu Ala Val Ser Asn Phe Leu Thr Ala Leu Ser
            275                 280                 285

Leu Gln Arg Lys Ser Arg Asn Gln Gln Val Pro His Pro Ala Ile
            290                 295                 300

Ser Gly Asn Ile Trp Ala Ala Leu Arg Ile Ala Leu Ser Leu Met Asp
305                 310                 315                 320

Gln Pro Glu Leu Phe Gln Ala Ala Asn Leu Gly Asp Leu Asp Val Leu
                325                 330                 335

Leu Arg Ala Phe Asn Leu Asp Pro
            340
```

<210> SEQ ID NO 7
<211> LENGTH: 344
<212> TYPE: PRT
<213> ORGANISM: Artificial
<220> FEATURE:
<223> OTHER INFORMATION: Mus musculus TPR3-N13A TRIP8b Variant

<400> SEQUENCE: 7

```
Met Gln Ala Glu Trp Glu Glu Met Ala Arg Arg Asn Trp Ile Ser Glu
1               5                  10                  15
```

```
Asn Gln Glu Ala Gln Asn Gln Val Thr Val Ser Ala Ser Glu Lys Gly
            20                  25                  30

Tyr Tyr Phe His Thr Glu Asn Pro Phe Lys Asp Trp Pro Gly Ala Phe
        35                  40                  45

Glu Glu Gly Leu Lys Arg Leu Lys Glu Gly Asp Leu Pro Val Thr Ile
50                  55                  60

Leu Phe Met Glu Ala Ala Ile Leu Gln Asp Pro Gly Asp Ala Glu Ala
65                  70                  75                  80

Trp Gln Phe Leu Gly Ile Thr Gln Ala Glu Asn Glu Asn Glu Gln Ala
                85                  90                  95

Ala Ile Val Ala Leu Gln Arg Cys Leu Glu Leu Gln Pro Asn Asn Leu
            100                 105                 110

Lys Ala Leu Met Ala Leu Ala Val Ser Tyr Thr Ala Thr Ser His Gln
        115                 120                 125

Gln Asp Ala Cys Glu Ala Leu Lys Asn Trp Ile Lys Gln Asn Pro Lys
    130                 135                 140

Tyr Lys Tyr Leu Val Lys Asn Lys Lys Gly Ser Pro Gly Leu Thr Arg
145                 150                 155                 160

Arg Met Ser Lys Ser Pro Val Asp Ser Ser Val Leu Glu Gly Val Lys
                165                 170                 175

Glu Leu Tyr Leu Glu Ala Ala His Gln Asn Gly Asp Met Ile Asp Pro
            180                 185                 190

Asp Leu Gln Thr Gly Leu Gly Val Leu Phe His Leu Ser Gly Glu Phe
        195                 200                 205

Asn Arg Ala Ile Asp Ala Phe Asn Ala Ala Leu Thr Val Arg Pro Glu
    210                 215                 220

Asp Tyr Ser Leu Trp Asn Arg Leu Gly Ala Thr Leu Ala Asn Gly Asp
225                 230                 235                 240

Arg Ser Glu Glu Ala Val Ala Tyr Thr Arg Ala Leu Glu Ile Gln
                245                 250                 255

Pro Gly Phe Ile Arg Ser Arg Tyr Asn Leu Gly Ile Ser Cys Ile Asn
            260                 265                 270

Leu Gly Ala Tyr Arg Glu Ala Val Ser Asn Phe Leu Thr Ala Leu Ser
        275                 280                 285

Leu Gln Arg Lys Ser Arg Asn Gln Gln Val Pro His Pro Ala Ile
    290                 295                 300

Ser Gly Asn Ile Trp Ala Ala Leu Arg Ile Ala Leu Ser Leu Met Asp
305                 310                 315                 320

Gln Pro Glu Leu Phe Gln Ala Ala Asn Leu Gly Asp Leu Asp Val Leu
                325                 330                 335

Leu Arg Ala Phe Asn Leu Asp Pro
            340

<210> SEQ ID NO 8
<211> LENGTH: 344
<212> TYPE: PRT
<213> ORGANISM: Artificial
<220> FEATURE:
<223> OTHER INFORMATION: Mus musculus TPR2-E15K TRIP8b Variant

<400> SEQUENCE: 8

Met Gln Ala Glu Trp Glu Glu Met Ala Arg Arg Asn Trp Ile Ser Glu
1               5                   10                  15

Asn Gln Glu Ala Gln Asn Gln Val Thr Val Ser Ala Ser Glu Lys Gly
            20                  25                  30
```

```
Tyr Tyr Phe His Thr Glu Asn Pro Phe Lys Asp Trp Pro Gly Ala Phe
             35                  40                  45

Glu Glu Gly Leu Lys Arg Leu Lys Glu Gly Asp Leu Pro Val Thr Ile
 50                  55                  60

Leu Phe Met Glu Ala Ala Ile Leu Gln Asp Pro Gly Asp Ala Glu Ala
 65                  70                  75                  80

Trp Gln Phe Leu Gly Ile Thr Gln Ala Glu Asn Lys Asn Glu Gln Ala
                 85                  90                  95

Ala Ile Val Ala Leu Gln Arg Cys Leu Glu Leu Gln Pro Asn Asn Leu
                100                 105                 110

Lys Ala Leu Met Ala Leu Ala Val Ser Tyr Thr Asn Thr Ser His Gln
                115                 120                 125

Gln Asp Ala Cys Glu Ala Leu Lys Asn Trp Ile Lys Gln Asn Pro Lys
130                 135                 140

Tyr Lys Tyr Leu Val Lys Asn Lys Gly Ser Pro Gly Leu Thr Arg
145                 150                 155                 160

Arg Met Ser Lys Ser Pro Val Asp Ser Ser Val Leu Glu Gly Val Lys
                165                 170                 175

Glu Leu Tyr Leu Glu Ala Ala His Gln Asn Gly Asp Met Ile Asp Pro
                180                 185                 190

Asp Leu Gln Thr Gly Leu Gly Val Leu Phe His Leu Ser Gly Glu Phe
                195                 200                 205

Asn Arg Ala Ile Asp Ala Phe Asn Ala Ala Leu Thr Val Arg Pro Glu
                210                 215                 220

Asp Tyr Ser Leu Trp Asn Arg Leu Gly Ala Thr Leu Ala Asn Gly Asp
225                 230                 235                 240

Arg Ser Glu Glu Ala Val Glu Ala Tyr Thr Arg Ala Leu Glu Ile Gln
                245                 250                 255

Pro Gly Phe Ile Arg Ser Arg Tyr Asn Leu Gly Ile Ser Cys Ile Asn
                260                 265                 270

Leu Gly Ala Tyr Arg Glu Ala Val Ser Asn Phe Leu Thr Ala Leu Ser
                275                 280                 285

Leu Gln Arg Lys Ser Arg Asn Gln Gln Gln Val Pro His Pro Ala Ile
                290                 295                 300

Ser Gly Asn Ile Trp Ala Ala Leu Arg Ile Ala Leu Ser Leu Met Asp
305                 310                 315                 320

Gln Pro Glu Leu Phe Gln Ala Ala Asn Leu Gly Asp Leu Asp Val Leu
                325                 330                 335

Leu Arg Ala Phe Asn Leu Asp Pro
            340

<210> SEQ ID NO 9
<211> LENGTH: 344
<212> TYPE: PRT
<213> ORGANISM: Artificial
<220> FEATURE:
<223> OTHER INFORMATION: Mus musculus TPR5-N5A TRIP8b Variant

<400> SEQUENCE: 9

Met Gln Ala Glu Trp Glu Glu Met Ala Arg Arg Asn Trp Ile Ser Glu
 1               5                  10                  15

Asn Gln Glu Ala Gln Asn Gln Val Thr Val Ser Ala Ser Glu Lys Gly
                20                  25                  30

Tyr Tyr Phe His Thr Glu Asn Pro Phe Lys Asp Trp Pro Gly Ala Phe
             35                  40                  45
```

Glu Glu Gly Leu Lys Arg Leu Lys Glu Gly Asp Leu Pro Val Thr Ile
            50                  55                  60

Leu Phe Met Glu Ala Ala Ile Leu Gln Asp Pro Gly Asp Ala Glu Ala
 65                  70                  75                  80

Trp Gln Phe Leu Gly Ile Thr Gln Ala Glu Asn Glu Asn Glu Gln Ala
                    85                  90                  95

Ala Ile Val Ala Leu Gln Arg Cys Leu Glu Leu Gln Pro Asn Asn Leu
                100                 105                 110

Lys Ala Leu Met Ala Leu Ala Val Ser Tyr Thr Asn Thr Ser His Gln
            115                 120                 125

Gln Asp Ala Cys Glu Ala Leu Lys Asn Trp Ile Lys Gln Asn Pro Lys
130                 135                 140

Tyr Lys Tyr Leu Val Lys Asn Lys Lys Gly Ser Pro Gly Leu Thr Arg
145                 150                 155                 160

Arg Met Ser Lys Ser Pro Val Asp Ser Ser Val Leu Glu Gly Val Lys
                165                 170                 175

Glu Leu Tyr Leu Glu Ala Ala His Gln Asn Gly Asp Met Ile Asp Pro
            180                 185                 190

Asp Leu Gln Thr Gly Leu Gly Val Leu Phe His Leu Ser Gly Glu Phe
            195                 200                 205

Asn Arg Ala Ile Asp Ala Phe Asn Ala Ala Leu Thr Val Arg Pro Glu
210                 215                 220

Asp Tyr Ser Leu Trp Ala Arg Leu Gly Ala Thr Leu Ala Asn Gly Asp
225                 230                 235                 240

Arg Ser Glu Glu Ala Val Glu Ala Tyr Thr Arg Ala Leu Glu Ile Gln
                245                 250                 255

Pro Gly Phe Ile Arg Ser Arg Tyr Asn Leu Gly Ile Ser Cys Ile Asn
            260                 265                 270

Leu Gly Ala Tyr Arg Glu Ala Val Ser Asn Phe Leu Thr Ala Leu Ser
            275                 280                 285

Leu Gln Arg Lys Ser Arg Asn Gln Gln Gln Val Pro His Pro Ala Ile
290                 295                 300

Ser Gly Asn Ile Trp Ala Ala Leu Arg Ile Ala Leu Ser Leu Met Asp
305                 310                 315                 320

Gln Pro Glu Leu Phe Gln Ala Ala Asn Leu Gly Asp Leu Asp Val Leu
                325                 330                 335

Leu Arg Ala Phe Asn Leu Asp Pro
            340

<210> SEQ ID NO 10
<211> LENGTH: 344
<212> TYPE: PRT
<213> ORGANISM: Artificial
<220> FEATURE:
<223> OTHER INFORMATION: Mus musculus TPR6-R2A TRIP8b Variant

<400> SEQUENCE: 10

Met Gln Ala Glu Trp Glu Met Ala Arg Arg Asn Trp Ile Ser Glu
 1               5                  10                  15

Asn Gln Glu Ala Gln Asn Gln Val Thr Val Ser Ala Ser Glu Lys Gly
            20                  25                  30

Tyr Tyr Phe His Thr Glu Asn Pro Phe Lys Asp Trp Pro Gly Ala Phe
                35                  40                  45

Glu Glu Gly Leu Lys Arg Leu Lys Glu Gly Asp Leu Pro Val Thr Ile
            50                  55                  60

```
Leu Phe Met Glu Ala Ala Ile Leu Gln Asp Pro Gly Asp Ala Glu Ala
 65              70                  75                  80

Trp Gln Phe Leu Gly Ile Thr Gln Ala Glu Asn Glu Asn Glu Gln Ala
                 85                  90                  95

Ala Ile Val Ala Leu Gln Arg Cys Leu Glu Leu Gln Pro Asn Asn Leu
                100                 105                 110

Lys Ala Leu Met Ala Leu Ala Val Ser Tyr Thr Asn Thr Ser His Gln
            115                 120                 125

Gln Asp Ala Cys Glu Ala Leu Lys Asn Trp Ile Lys Gln Asn Pro Lys
            130                 135                 140

Tyr Lys Tyr Leu Val Lys Asn Lys Lys Gly Ser Pro Gly Leu Thr Arg
145                 150                 155                 160

Arg Met Ser Lys Ser Pro Val Asp Ser Ser Val Leu Glu Gly Val Lys
                165                 170                 175

Glu Leu Tyr Leu Glu Ala Ala His Gln Asn Gly Asp Met Ile Asp Pro
                180                 185                 190

Asp Leu Gln Thr Gly Leu Gly Val Leu Phe His Leu Ser Gly Glu Phe
            195                 200                 205

Asn Arg Ala Ile Asp Ala Phe Asn Ala Ala Leu Thr Val Arg Pro Glu
            210                 215                 220

Asp Tyr Ser Leu Trp Asn Arg Leu Gly Ala Thr Leu Ala Asn Gly Asp
225                 230                 235                 240

Arg Ser Glu Glu Ala Val Glu Ala Tyr Thr Arg Ala Leu Glu Ile Gln
                245                 250                 255

Pro Gly Phe Ile Ala Ser Arg Tyr Asn Leu Gly Ile Ser Cys Ile Asn
                260                 265                 270

Leu Gly Ala Tyr Arg Glu Ala Val Ser Asn Phe Leu Thr Ala Leu Ser
            275                 280                 285

Leu Gln Arg Lys Ser Arg Asn Gln Gln Gln Val Pro His Pro Ala Ile
            290                 295                 300

Ser Gly Asn Ile Trp Ala Ala Leu Arg Ile Ala Leu Ser Leu Met Asp
305                 310                 315                 320

Gln Pro Glu Leu Phe Gln Ala Ala Asn Leu Gly Asp Leu Asp Val Leu
                325                 330                 335

Leu Arg Ala Phe Asn Leu Asp Pro
                340
```